(12) United States Patent
Skoda

(10) Patent No.: US 11,275,070 B2
(45) Date of Patent: Mar. 15, 2022

(54) SYSTEMS AND METHODS FOR DIPSTICK DIAGNOSTIC TOOLS AND RELATED METHODS

(71) Applicant: Ahkeo Labs, LLC, Mayfield Village, OH (US)

(72) Inventor: Brent M. Skoda, Irving, TX (US)

(*) Notice: Subject to any disclaimer, the term of this patent is extended or adjusted under 35 U.S.C. 154(b) by 645 days.

(21) Appl. No.: 15/843,916

(22) Filed: Dec. 15, 2017

(65) Prior Publication Data
US 2018/0356386 A1     Dec. 13, 2018

Related U.S. Application Data

(63) Continuation of application No. 15/144,021, filed on May 2, 2016, now abandoned.
(Continued)

(51) Int. Cl.
*G01N 33/15* (2006.01)
*A61M 11/04* (2006.01)
(Continued)

(52) U.S. Cl.
CPC ............ *G01N 33/15* (2013.01); *A61B 5/082* (2013.01); *A61M 11/041* (2013.01);
(Continued)

(58) Field of Classification Search
CPC . G01N 33/15; A61M 15/0003; A61M 11/041; A61M 2205/3303; A61M 2205/3553; A61M 2205/3569; A61M 2205/3592; A61M 2205/6018; A61M 2205/50; A61M 2205/52; A61M 2205/3584; A61M 2205/8206; A61M 2205/18; A61M 2205/702; A61M 2205/502; A61B 5/1455; A61B 5/1468; A61B 5/4845; A61B 5/4866; A61B 5/7275; A61B 5/4836; A61B 5/082; A61B 5/0071; A61B 5/0075; A61B 5/01; A61B 5/073;
(Continued)

(56) References Cited

U.S. PATENT DOCUMENTS 7,219,665 B1 * 5/2007 Braithwaite ...... A61M 15/0048
128/203.21
2003/0200964 A1 * 10/2003 Blakley ............. A61M 15/0066
128/200.23
(Continued)

OTHER PUBLICATIONS

U.S. Office Action on U.S. Appl. No. 15/144,021 dated Jun. 16, 2017.

*Primary Examiner* — Peter J Macchiarolo
*Assistant Examiner* — John M Royston
(74) *Attorney, Agent, or Firm* — Foley & Lardner LLP

(57) ABSTRACT

The present disclosure relates to a medical diagnostic and delivery device includes a dipstick type device. The device include cartridge containing one more substance or medicaments configured to be delivered to a user in the form a liquid, particles, or fine mist. In particular embodiments, the device can include a heating element to vaporize the substance and deliver the vapor to a user. In various embodiments, the device includes one or more sensors configured to analyze the one or substances or medications contained within the cartridge and sense, detect or otherwise determine an expiration date of the substance or medication.

14 Claims, 18 Drawing Sheets

Related U.S. Application Data

(60) Provisional application No. 62/155,841, filed on May 1, 2015.

(51) Int. Cl.
  A61M 15/00 (2006.01)
  A61B 5/00 (2006.01)
  A61B 5/145 (2006.01)
  A61B 5/1455 (2006.01)
  A61B 5/1468 (2006.01)
  A61B 5/08 (2006.01)
  *A61B 5/01* (2006.01)
  *A61B 5/07* (2006.01)
  *A61B 5/083* (2006.01)

(52) U.S. Cl.
  CPC ....... *A61M 15/0003* (2014.02); *A61B 5/0071* (2013.01); *A61B 5/0075* (2013.01); *A61B 5/01* (2013.01); *A61B 5/073* (2013.01); *A61B 5/083* (2013.01); *A61B 5/1455* (2013.01); *A61B 5/1468* (2013.01); *A61B 5/14507* (2013.01); *A61B 5/14532* (2013.01); *A61B 5/14546* (2013.01); *A61B 5/4845* (2013.01); *A61B 5/4866* (2013.01); *A61B 5/7275* (2013.01); *A61M 2205/18* (2013.01); *A61M 2205/3303* (2013.01); *A61M 2205/3553* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/6018* (2013.01); *A61M 2205/702* (2013.01); *A61M 2205/8206* (2013.01)

(58) Field of Classification Search
  CPC . A61B 5/083; A61B 5/14507; A61B 5/14532; A61B 5/14546
  See application file for complete search history.

(56) References Cited

U.S. PATENT DOCUMENTS

| | | | |
|---|---|---|---|
| 2005/0268911 A1* | 12/2005 | Cross | A61M 11/002 128/204.17 |
| 2008/0199894 A1* | 8/2008 | Galasso | G16H 40/67 435/14 |
| 2010/0211005 A1* | 8/2010 | Edwards | A61P 5/28 604/82 |
| 2016/0022541 A1* | 1/2016 | Dalal | A61J 7/0418 221/9 |

* cited by examiner

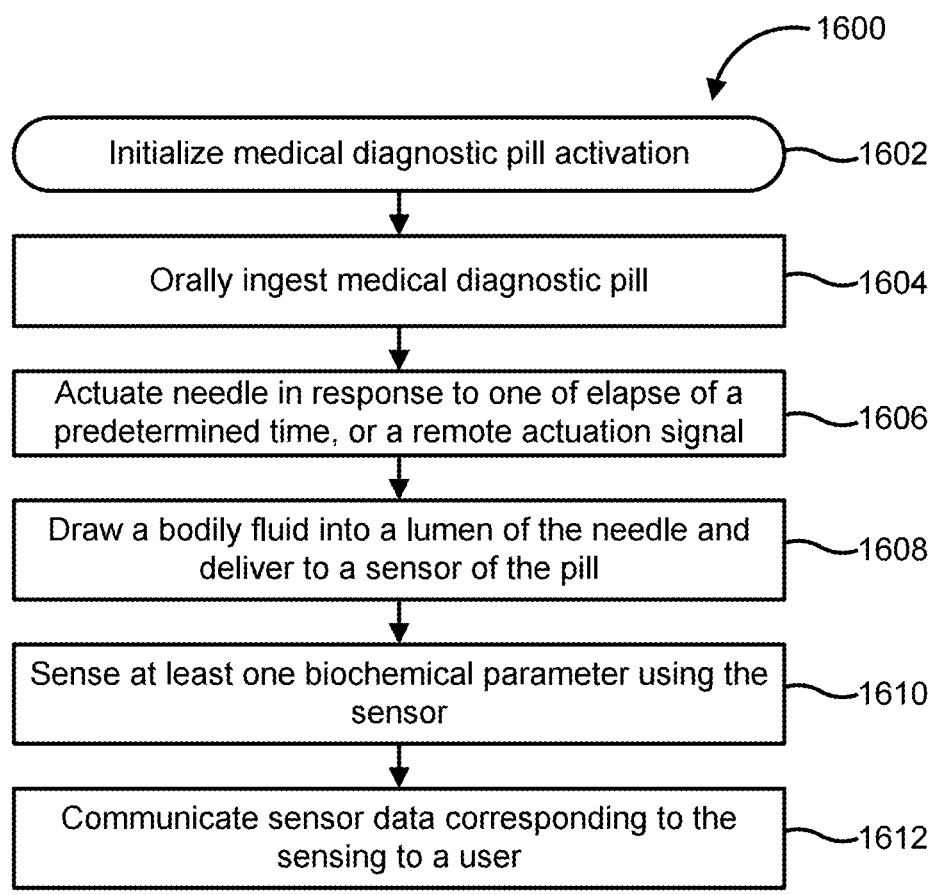

SYSTEMS AND METHODS FOR DIPSTICK DIAGNOSTIC TOOLS AND RELATED METHODS

RELATED APPLICATIONS

The present application is a continuation application of U.S. Ser. No. 15/144,021, titled "SYSTEMS AND METHODS FOR DIPSTICK DIAGNOSTIC TOOLS AND RELATED METHODS" and filed May 2, 2016, which application claims the benefit of and priority to U.S. Provisional Application No. 62/155,841, titled "SYSTEMS AND METHODS FOR DIPSTICK DIAGNOSTIC TOOLS AND RELATED METHODS" and filed May 1, 2015, the entire contents of both are hereby incorporated by reference.

TECHNICAL FIELD

The present application relates generally to systems and methods for medical diagnostics and medication delivery.

BACKGROUND

A central theme in medical diagnostics is the ability to diagnose one or more medical conditions at the point of care. The human body presents various bodily fluids which can be accessible in a non-invasive manner such as, for example, breath, saliva, tears, mucus, etc. which can contain key biomarkers or analytes for providing an accurate analysis of a medical condition. For example, biomarkers such as glucose, alcohol, cancer biomarkers, biomarkers of stress, pregnancy, polycystic ovary syndrome (PCOS), neurological diseases (e.g., Cushing's disease, Addison's diseases, Alzhiemers, multiple schlerosis (MS), post-traumatic stress disorder (PTSD), Parkinson's disease, etc.), metabolic diseases, osteoporosis, and other diseases can present themselves in bodily fluids.

Vaporizers or inhalers may be used to administer, transform or otherwise dispense a substance in a consumable format (i.e. vapor, fine powder, mist, liquid) for the user. One form of vaporizers includes electronic cigarettes. The substance for consumption through a vaporizer or vaporization apparatus or device may include Caffeine, an energy boosting formulation, a flavored substance, a medicinal formula, a supplement, a vitamin, a mineral, any ingredient officially monographed and listed in the Homeopathic Pharmacopeia of the United States of America (the "HPUS"), or various other products for consumption alone or in combination.

SUMMARY

Embodiments described herein relate generally to medical diagnosis and delivery devices, and in particular to dipstick type medical diagnostic devices or ingestible pills for providing one or more diagnostic or substance delivery application.

In some embodiments, a medical diagnostic and delivery device includes a dipstick type device. The device include cartridge containing one more substance or medicaments configured to be delivered to a user in the form a liquid, particles, or fine mist. In particular embodiments, the device can include a heating element to vaporize the substance and deliver the vapor to a user. In various embodiments, the device includes one or more sensors configured to analyze the one or substances or medications contained within the cartridge and sense, detect or otherwise determine an expiration date of the substance or medication. The sensor can include for example, a colorimetric sensor (e.g., a lateral flow sensor, a paper microfluidics based sensor, a microfluidic reactor, etc.), an electrochemical sensor (e.g., a redox sensor, an impedance sensor, a conductance sensor), an electromagnetic sensor, a nanopore device, or any other suitable sensor. The cartridge can be in fluid communication with the sensor. In other embodiments, the device can also detect the presence of harmful substances in the substance or medication which become incorporated in the substance or medication during a manufacturing process thereby preventing delivery of the contaminated substance to the user. In various embodiments, the sensor is removably coupled to the device and can be disposable. Once a sensing operation has been performed, the used sensor can be removed from the medical device and a new sensor can be inserted into the device to replace the old sensor. In other words, a fresh sensor is used for each measurement. In various embodiments, the medical device is configured to receive a variety of sensors such that each of the variety of sensors is configured to sense, detect or otherwise determine different physical or biochemical parameters of a substance or a bodily fluid inserted into the medical device. In some embodiments, the cartridge can include a plurality of silos, chambers, channels, containers, among others. Each of the silos can contain a plurality of the same medication or different medications. In one embodiment, the cartridge includes a laterally displaceable cartridge having a plurality of substance silos arranged along a lateral axis of the cartridge. In another embodiment, the cartridge includes a circular cartridge including a plurality of substance silos positioned in radial orientation about a central axis of the cartridge. The circular cartridge is configured to be rotated about its central axis to position a predetermined substance for analysis or delivery to the user.

The device also includes electronic circuitry that can include one or more of a power source, a processor, a memory, a speaker, microphone and a display. The processor may be configured to execute instructions for analyzing signals provided by the sensor and determine expiry of the substance, presence of harmful contaminants in the medication, and/or identify correct substance to be delivered to the user. The electronic circuitry can also include communication and/or location devices such as Bluetooth®, Wi-Fi, RFID, cellular transceiver, and/or GPS. In various embodiments, a medical provider (e.g., a doctor, a nurse, a caregiver, or a specially programmer remote server such as a smartphone, a tablet, a remote computer, etc.) can communicate with the medical device using one or more of the communication devices included in the electronic circuitry to remotely monitor the status (e.g., expiry status, presence of harmful contaminants, identify correct medication to be delivery) of the one or more substance contained within the cartridge, and select one or more medications within the cartridge to be delivered to the user.

In various embodiments, the medical diagnostic device can include a miniature sensor embedded within the cartridge of the medical device. The sensor can be positioned inside one or more silos included in the cartridge that contain a liquid substance. The sensor can be configured to sense if the substance has expired, sense the presence of contaminants in the substance, or sense if the substance has decomposed(e.g., decomposition or degradation of the substance such as insulin, albuterol, fluticasone, or any other substance due to heat or light). The sensor can include an electrochemical sensor, or a grid/matrix type sensor such as a lateral flow sensor, a paper or polymeric sensor positioned within one or more silos of the cartridge. The sensor can be configured to provide information of the level of the substance remaining in the silo regardless of a physical orientation of the device.

In various embodiments, the device can be configured to sense or otherwise determine a level of substance remaining in the cartridge. In some embodiments, the device can determine a level of substance remaining in the cartridge using battery power consumption. In such embodiments, a fully charged battery and a cartridge include the substance or medications are coupled to the device. Medication is dispensed from the medical device at a controlled flow rate. An amount of battery power consumed for dispensing the medication is determined and a level of substance present in the cartridge is determined based on the battery power consumed.

In various embodiments, if the level of the substance in the cartridge falls below a critical level, the device indicates to a user, for example, via an audio/visual indication or an alert communicated to a remote server (e.g., an SMS message, an alert on a smartphone or tablet app, or an alert on a remote computer) to inform the user the substance level is critically low. In some embodiments, the critical level can be based on a dosage of the substance consumed by the user.

In some embodiments, a dipstick type medical diagnostic device is configured to receive a breath of a user and sense, detect or otherwise determine one or more physical and biochemical parameters of the breath which are indicative of the health of the user. In other embodiments, the device can also be used to receive and analyze saliva of a user. Such a medical diagnostic device can include a first channel into which a user can blow. One or more sensors, for example, electrochemical or colorimetric sensors are included in the medical device and configured to detect one or more physical or biochemical parameters of the patient (glucose, flu virus, other viruses, bacteria, or any other biomarkers of disease). The medical device includes a cartridge including a plurality of therapeutic substances. A processor included in the medication device includes instructions to interpret the signal generated by the sensor for performing a diagnosis of a medical condition of the patient. Based on the diagnosis, the processor is configured to identify one or more suitable medications included in the cartridge to be delivered to the user. The processor can determine a cartridge position which will provide the identified medication to the user, displace the cartridge to position the cartridge within the device such that the identified medication can be delivered to the user via the first channel or a second channel included in the device.

In various embodiments, a cartridge of the medical device can include a sensor configured to measure blood alcohol concentration (BAC) from a breath of a user, or any other health parameter of the user. In various embodiments, the sensor can include one or more of a breathalyzer, an infrared sensor for detecting alcohol concentration, or an electrochemical sensor for example an alcohol oxidase based electrochemical sensor. A processor can determine an amount of a masking substance to be delivered to the user to mask or otherwise lower the BAC level of the user. Based on the determination, the device is configured to deliver a sufficient amount of a substance to the user to mask or otherwise lower the user BAC level. In other embodiments, the device can also be used to perform a medical diagnostic (e.g., determine blood glucose levels, diagnose viral or bacterial infections, etc.) and determine an appropriate amount of medication to be delivered to the user. In particular embodiments, the device can also include one or more communication devices such as Bluetooth®, RFID, Wi-Fi, cellular transceivers or any other communication device to record a medical diagnosis or log date, time and/or quantity of substance delivery. The record can be included in an app (e.g., a smartphone or tablet app) which is configured for health monitoring and analyze user health trends over an extended period of time.

In various embodiments in which the substance is delivered as a vapor, the medical device provides a vaporization device configured to vaporize a plurality of substances independently or collectively as selected. The plurality of substance includes a plurality of independently stored liquids, for example, contained in a single multi-content cartridge. The vaporization device may be configured to heat one or more of the liquids independently and to vary which one or more of the liquids is heated at any time to allow a user to switch substances for vaporization and or combine different vapors. The vaporization device may be configured to heat different substances for different durations based on the type of substance. At least one of the device or the multi-substance cartridge may be configured to identify or determine the substances provided in the cartridge and to permit a user selection of the substances for consumption through inhaling via an outlet channel in the device.

In various embodiments, a dipstick type medical diagnostic device includes a temperature sensor and is configured to be positioned within a buccal cavity of a patient analogous to a thermometer. The device also includes a fluid communication channel (e.g., a lateral flow substrate or a paper microfluidic channel) configured to receive a saliva of a user. The device also includes a sensor to analyze the saliva and sense one or more physical or biochemical parameters of the user. Such parameters can include glucose level, BAC, adrenal conditions (e.g., Cushing's disease, Addison's disease), hormone levels, altered female hormone states (e.g., PCOS, menopause, anovulation, pregnancy, irregular period cycles), altered male hormone states (e.g., hypogonadism, andropause, hyperestrogenic states), metabolic disorders (e.g., insulin resistance, diabetes, muscular dystrophy) benign and metastatic neoplasms (e.g., breast cancer, pancreatic cancer, prostate cancer, oral cancer, lung and throat cancer, etc.), infection diseases (e.g., HIV, viral hepatitis, flu, H1N1 flu, SARS virus, amoebiasis, heliobacter pylori infections, C. difficius infections, strep throat), food allergy, cortisol levels as indicators of stress, progesterone, or any other disease or medical condition for a which a biomarker is expressed in the saliva of a patient. The device can also include a processor, power source, audio/visual display and communication devices as described herein. In various embodiments, the saliva measurement device can have the form factor of a dental retainer, a dental brace or a mouth guard, which can be positioned within the buccal cavity of the user for extended periods of time to perform the sensing and diagnosis functions described herein.

In various embodiments, a medical device includes an ingestible pill for sensing one or more physical or biochemical parameters of a user such as, blood alcohol, blood glucose, stomach acidity, oral or stomach ulcers, or any other medical condition described herein. The pill can include a housing having a form factor of a pill and defining an internal volume. Electronic circuitry is positioned within the internal volume which can include a power source, a sensor, at least one communication device (e.g., a Bluetooth® device), and a processor. In one embodiment, the housing of the device can be biodegradable such that the housing dissolves to expose the electronic circuitry to the stomach contents and acids of a user. In such embodiments, each of the components included in the electronic circuitry can also be formed from food grade and/or organic materials which are bio-degradable or bio-consumable. In one embodiment, the power source is configured to generate power through an electrochemical reaction with stomach acids that produces electrons or ions for powering the electronic circuitry. The sensor can analyze the digestive fluids (e.g., stomach acids or intestinal digestive byproducts) to sense the physical or biochemical parameters.

In various embodiments, the processor can be configured to execute instructions to analyze the sensor data and communicate data corresponding to the analysis via the communication device (e.g., Bluetooth®) to the user (e.g., a smartphone or tablet app, or a remote server). The device can be formed from materials or coated with protective coatings (e.g., sol-gels, hydrogels or polymers) which prevent the device from being completely decomposing until the physical or biochemical parameter have been sensed and data communicated to the user. In other embodiments, the housing of the device is non-biodegradable. In such embodiments, the device includes a fluidic channel such as a capillary for drawing in a bodily fluid such as saliva or stomach acids to perform the diagnostic measurement. In still other embodiments, the device can include a microneedle, which can be activated by a plunger included in the device at a predetermined time after ingestion or by a remote actuation command. The needle is inserted into an endothelial layer of the digestive tract of the user to draw a small quantity of blood which is fluidly communicated to the sensor for sensing the physical or biochemical parameters of the user.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The skilled artisan will understand that the drawings primarily are for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

FIG. 16 is a schematic flow diagram of a method for performing a medical diagnosis using the medical diagnostic device of FIG. 16.

The features and advantages of the inventive concepts disclosed herein will become more apparent from the detailed description set forth below when taken in conjunction with the drawings.

DETAILED DESCRIPTION

Following below are more detailed descriptions of various concepts related to, and embodiments of, inventive variable counterweight systems and methods of operating variable counterweight systems. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Section A describes a network environment and computing environment which may be useful for practicing various computing related embodiments described herein.

Section B describes systems and methods of providing medical diagnosis and medicine administration via medical diagnostic and medicine administration devices.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

A. Computing and Network Environment

Figure 1A:
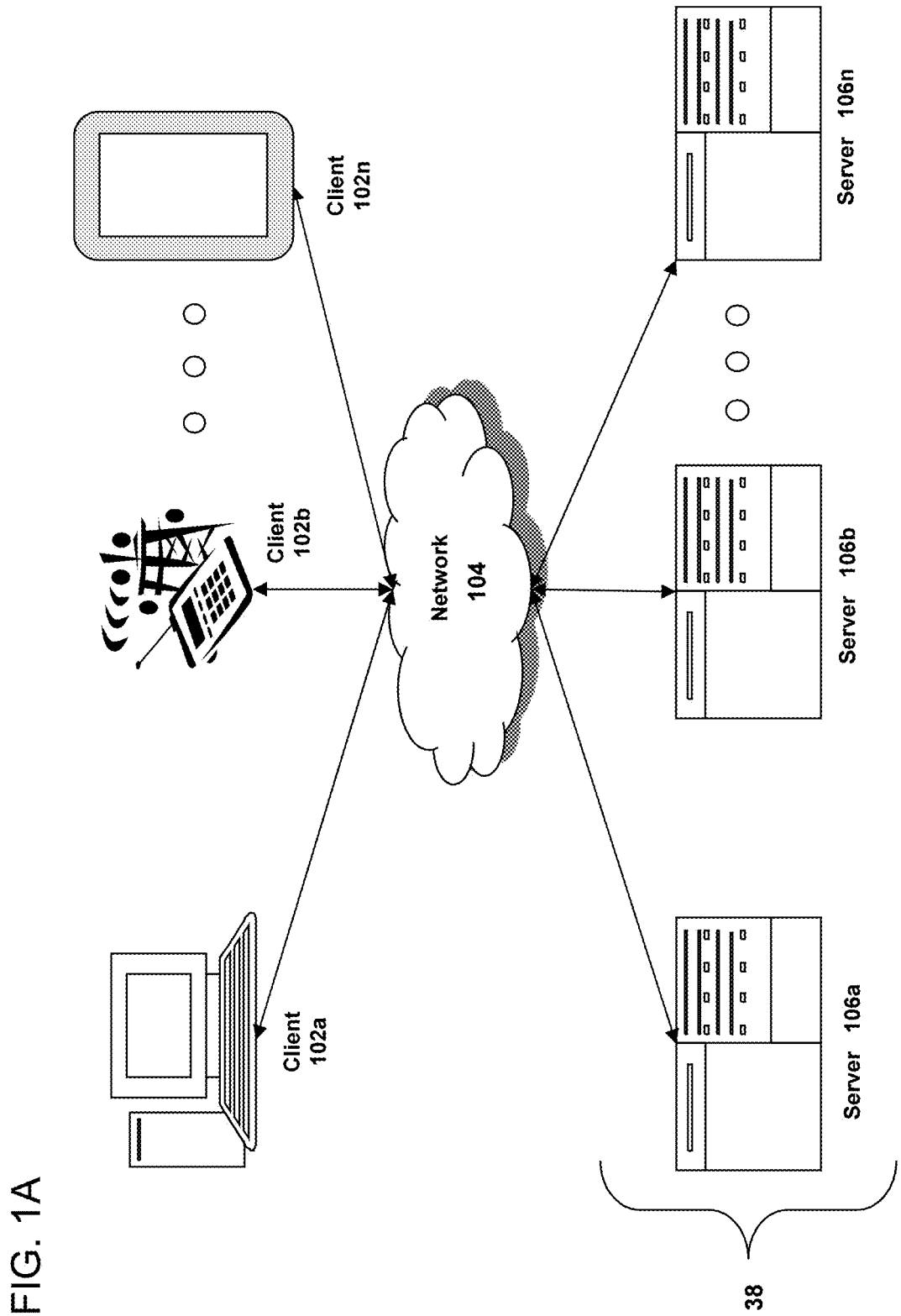
FIG. 1A is a block diagram depicting an embodiment of a network environment comprising client devices in communication with server devices.

Prior to discussing specific inventive embodiments, it may be helpful to describe aspects of the operating environment as well as associated system components (e.g., hardware elements) in connection with the methods and systems described herein. Referring to FIG. 1A, an embodiment of a network environment is depicted. In brief overview, the illustrated exploring network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although FIG. 1A shows a network 104 between the clients 102 and the servers 106, the clients 102 and the servers 106 may be on the same network 104. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, NFC, RFID Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network, which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the system may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Wash.), while one or more of the other servers 106 can operate on according to another type of operating system platform (e.g., Unix, Linux, or Mac OS X).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualized physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store.

Server 106 may be a file server, application server, web server, proxy server, appliance, network appliance, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

Figure 1B:
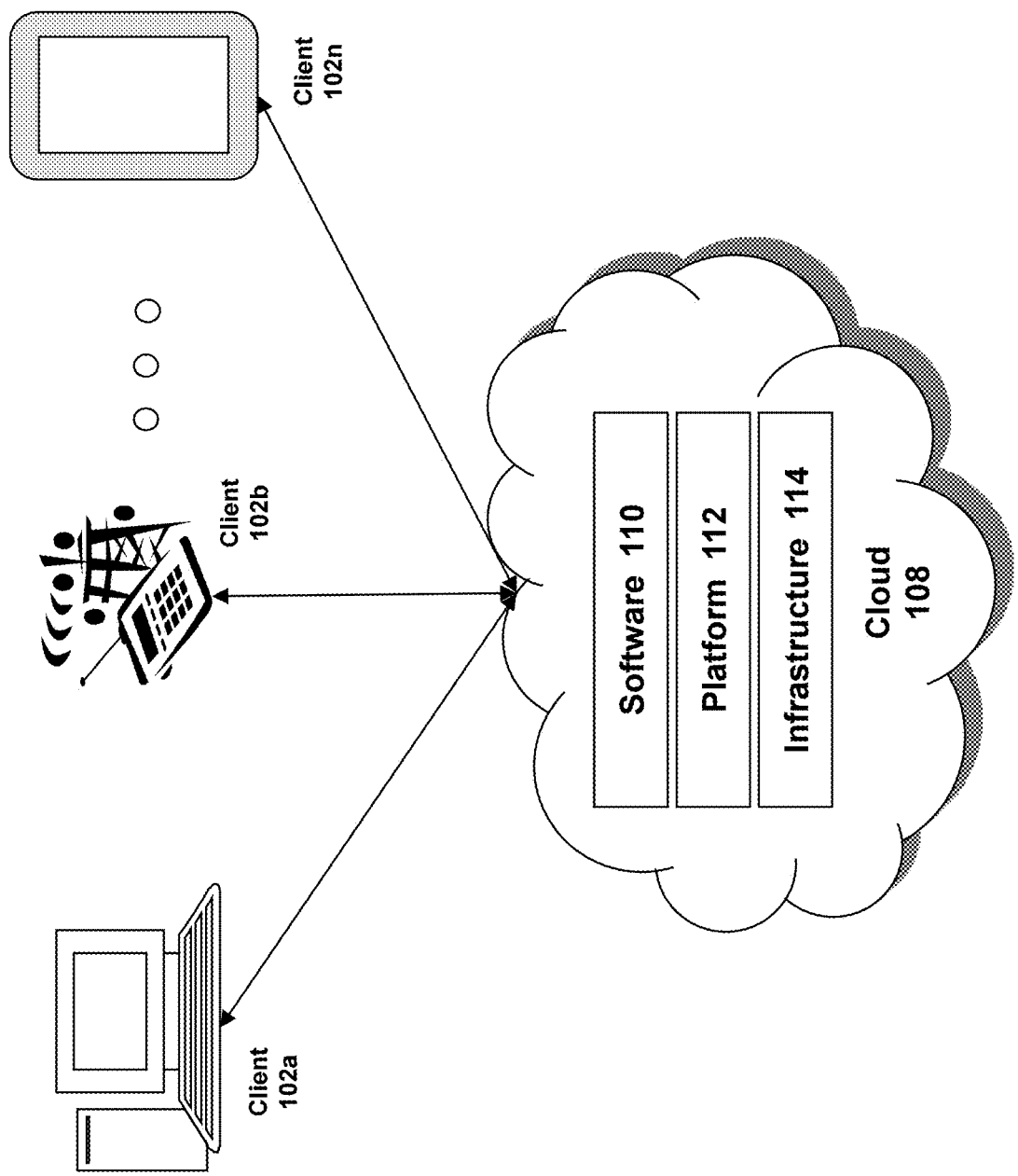
FIG. 1B is a block diagram depicting a cloud computing environment comprising client devices in communication with a cloud service provider.

Referring to FIG. 1B, a cloud computing environment is depicted. A cloud computing environment may provide client 102 with one or more resources provided by a network environment. The cloud computing environment may include one or more clients 102a-102n, in communication with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Wash., RACKSPACE CLOUD provided by Rackspace US, Inc., of San Antonio, Tex., Google Compute Engine provided by Google Inc. of Mountain View, Calif., or RIGHTSCALE provided by RightScale, Inc., of Santa Barbara, Calif. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, Calif., or OFFICE 365 provided by Microsoft Corporation. Examples of SaaS may also include data storage providers, e.g. DROPBOX provided by Dropbox, Inc. of San Francisco, Calif., Microsoft SKYDRIVE provided by Microsoft Corporation, Google Drive provided by Google Inc., or Apple ICLOUD provided by Apple Inc. of Cupertino, Calif.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, Calif.). Clients 102 may also access SaaS resources through smartphone or tablet applications, including, e.g., Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1C:
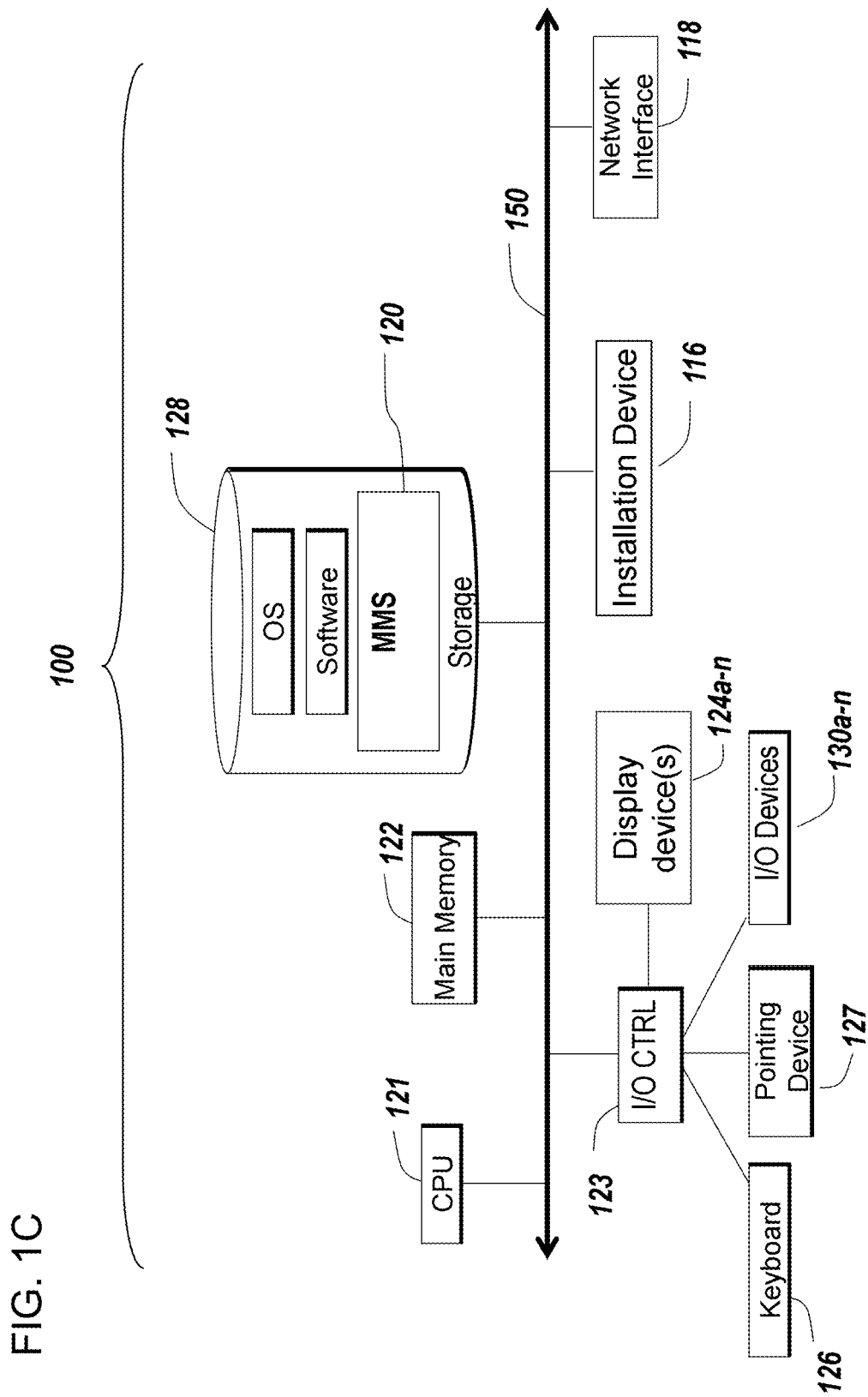
FIGS. 1C and 1D are block diagrams depicting embodiments of computing devices useful in connection with the methods and systems described herein.
Figure 1D:
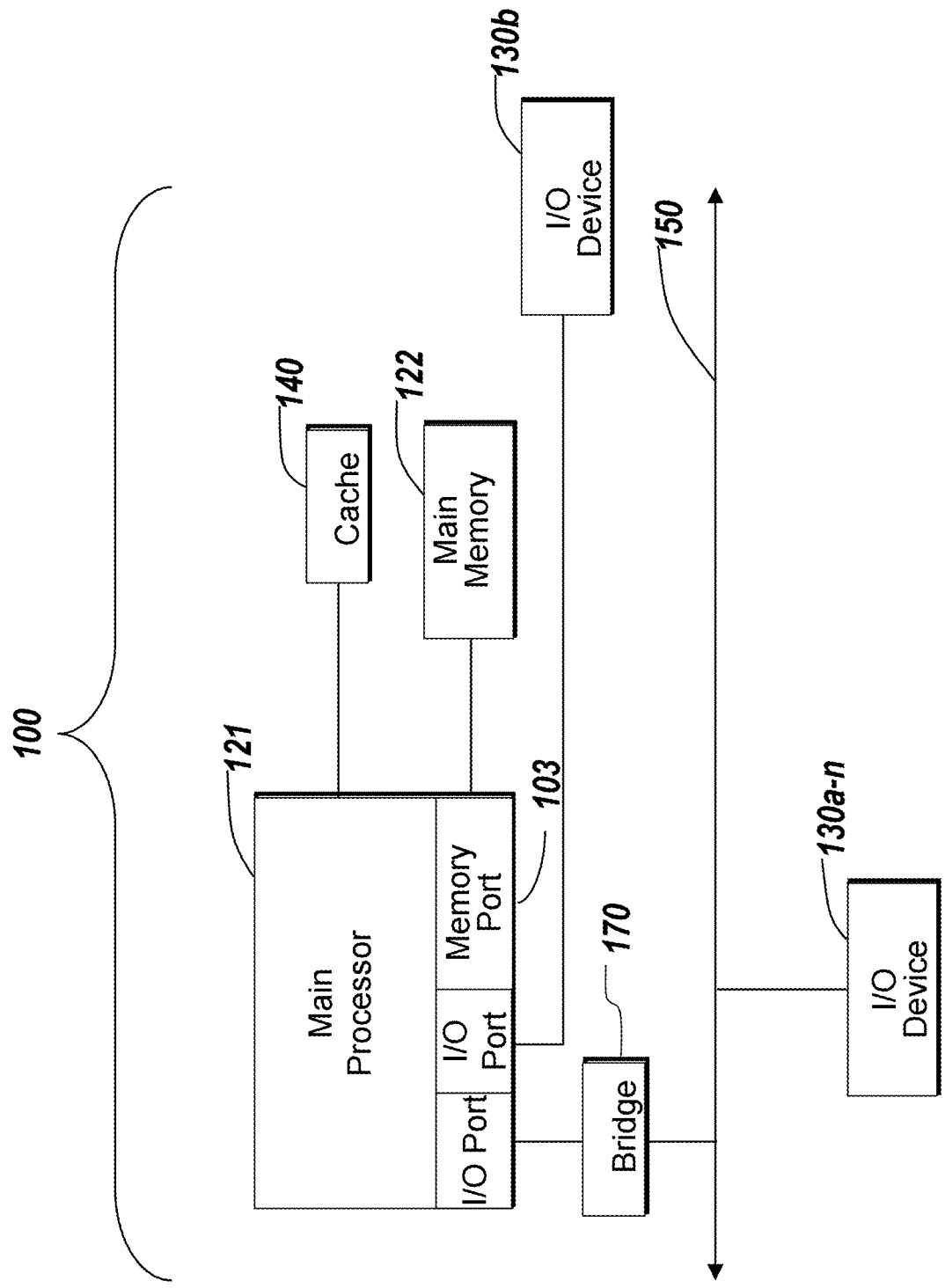

The client 102 and server 106 may be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an embodiment of the client 102 or a server 106. As shown in FIGS. 1C and 1D, each computing device 100 includes a central processing unit 121, and a main memory unit 122. As shown in FIG. 1C, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, and/or software of a medical diagnostic system 120 (e.g., the medical diagnostic device 200, 700, 900, 1200, 1300, 1400, 1500 or any other medical diagnostic device described herein). As shown in FIG. 1D, each computing device 100 may also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1C, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 may be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1D depicts an embodiment of a computer 100 in which the main processor 121 communicates directly with I/O device 130b or other processors 121' via HYPERTRANSPORT, RAPIDIO, or INFINIBAND communications technology. FIG. 1D also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 130a-130n may include a combination of multiple input or output devices, including, e.g., Microsoft KINECT, Nintendo Wiimote for the WII, Nintendo WII U GAMEPAD, or Apple IPHONE. Some devices 130a-130n allow gesture recognition inputs through combining some of the inputs and outputs. Some devices 130a-130n provides for facial recognition which may be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touch-screen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touch-screen devices, including, e.g., Microsoft PIXELSENSE or Multi-Touch Collaboration Wall, may have larger surfaces, such as on a table-top or on a wall, and may also interact with other electronic devices. Some I/O devices 130a-130n, display devices 124a-124n or group of devices may be augment reality devices. The I/O devices may be controlled by an I/O controller 123 as shown in FIG. 1C. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 124a-124n may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 124a-124n may also be a head-mounted display (HMD). In some embodiments, display devices 124a-124n or the corresponding I/O controllers 123 may be controlled through or have hardware support for OPENGL or DIRECTX API or other graphics libraries.

In some embodiments, the computing device 100 may include or connect to multiple display devices 124a-124n, which each may be of the same or different type and/or form. As such, any of the I/O devices 130a-130n and/or the I/O controller 123 may include any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may include multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices 100a or 100b connected to the computing device 100, via the network 104. In some embodiments software may be designed and constructed to use another computer's display device as a second display device 124a for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124a-124n.

Referring again to FIG. 1C, the computing device 100 may comprise a storage device 128 (e.g. one or more hard disk drives or redundant arrays of independent disks) for storing an operating system or other related software, and for storing application software programs such as any program related to the software 120 for the vaporization system. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage device 128 may be external and connect to the computing device 100 via an I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as an installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102a-102n may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a gaming system. For example, the computer system 100 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Wash.

In some embodiments, the computing device 100 is a digital audio player such as the Apple IPOD, IPOD Touch, and IPOD NANO lines of devices, manufactured by Apple Computer of Cupertino, Calif. Some digital audio players may have other functionality, including, e.g., a gaming system or any functionality made available by an application from a digital application distribution platform. For example, the IPOD Touch may access the Apple App Store. In some embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 100 is a tablet e.g. the IPAD line of devices by Apple; GALAXY TAB family of devices by Samsung; or KINDLE FIRE, by Amazon.com, Inc. of Seattle, Wash. In other embodiments, the computing device 100 is an eBook reader, e.g. the KINDLE family of devices by Amazon.com, or NOOK family of devices by Barnes & Noble, Inc. of New York City, N.Y.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call. In some embodiments, the communication device 102 is a wearable mobile computing device including but not limited to Google Glass and Samsung Gear.

In some embodiments, the status of one or more machines 102, 106 in the network 104 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the vaporization apparatus and related systems and methods disclosed herein.

Figure 2:
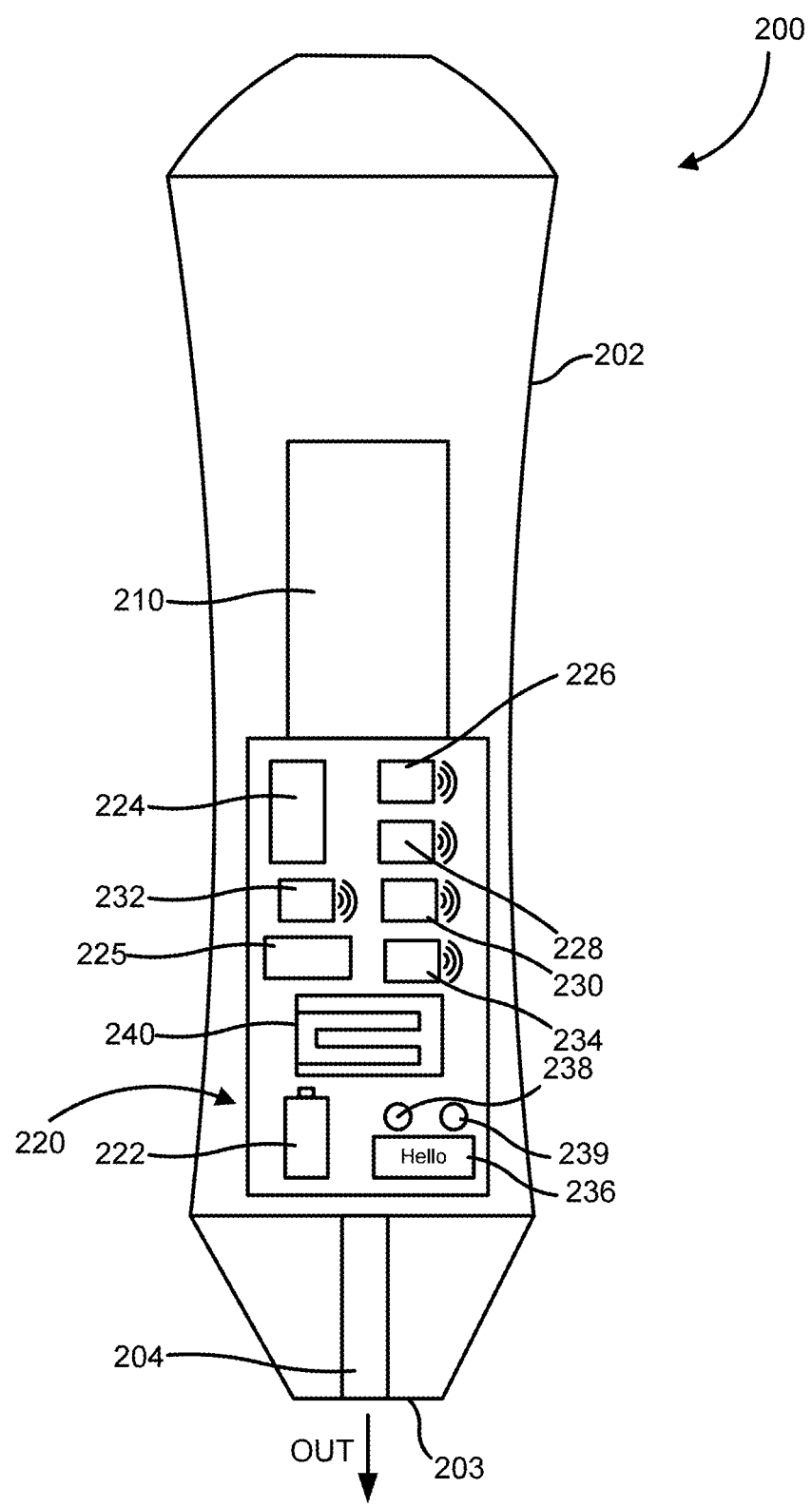
FIG. 2 is a front view of a medical diagnostic device according to an embodiment.

B. Systems and Methods of Providing Medical Diagnosis and Medicine Administration Via Medical Diagnostic and Medicine Administration Devices FIG. 2 is a front view of a medical diagnostic device 200 according to an embodiment. The device 200 includes a housing 202 defining an internal volume. FIG. 2 provides a partial cross-sectional view in the device 200. The device 200 includes a cartridge 210 containing a substance to be delivered to a user through a fluidic channel 204 defined at a proximal end 203 with respect to a user. For example, a user can position the proximal end 203 of the housing 202 on or near the lips of the user to inhale or draw the substance contained within the cartridge 210. While not shown, the device 200 can also include an injection system, for example, a plunger or a gas pump for delivering the substance orally to the user. In still other embodiments, device 200 can also include an injector needle to intramuscularly or intravenously deliver the substance to the user. The substance may be in the form of a liquid, a mist, powder, an aerosol or a vapor (e.g., as described with respect to the medical diagnostic device 300 described herein). The cartridge 210 can include a solid formulation that may be crushed, pulverized, or atomized, or heated and vaporized for inhalation. The cartridge 210 may include a substance including, but not limited to a medication, a drug, caffeine, panax, ginseng, gingko, biloba, bitter orage, cola-nut, guarana, natrum carbonicum, green tea, cocoa extract, cannabis, yerba mate, other vaporizable or inhalable supplements, pharmaceuticals, waxes, or liquids.

The cartridge 210 may include a cartridge identification code. The cartridge identification code may identify the substance (e.g., medication) contained in the cartridge, flavor identification, expiration information, or other pertinent information regarding the cartridge content.

The device includes electronic circuitry 220 for performing various sensing, diagnostic and data communication functions as may be necessary. The electronic circuitry 220 includes a power source 222, for example a DC battery, a AA battery, a AAA battery, a coin cell, a kinetic power generation device, a solar panel or any other power source. A processor 224 is included in the electronic circuitry 220.

The processor 224 is configured to execute instructions stored on a programmable memory 225 included in the electronic circuitry 220. The processor 224 is communicably coupled to a sensor 240 and configured to interpret signals provided by the sensor 240 included in the electronic circuitry 220, as described herein, to determine various parameters of the substance disposed within the cartridge. The interpreting can include comparing the signals using algorithms, look up tables, sensor calibration information, noise reduction or data filtering using instructions stored on the programmable memory 225. Such parameters can include determining if the substance (e.g., a medication) has expired or if harmful contaminants are present within the substance that can erroneously be introduced into the substance during a manufacturing process. Furthermore, the processor 224 may also be configured to identify a correct medication included in a plurality of medications disposed within the cartridge 210 for delivering to the user. In some embodiments, the electronic circuitry 220 can also include a counter to time the delivery of the substance(e.g., to determine a quantity delivered), an increment counter for each substance delivery suggestion, and/or to increment the counter each time a cartridge is changed.

The cartridge identification code may be electronically stored in the programmable memory 225, which programmable memory 225 may include other information such as historical usage information, including but not limited to location of use, device of use, time of use, or other data associated with the cartridge. The electronic circuitry 220 also includes a plurality of communication devices for receiving instruction from a user (e.g., input into an input interface (not shown) of the device 200, or communicated via a smart phone app, tablet app, remote server, etc.) or communicating information thereto.

For example, as shown in FIG. 2, the communication devices can include but are not limited to a Bluetooth® transceiver 226, a Wi-Fi transceiver 228, an RFID or NFC tag 230, and a cellular signal transceiver 232. The device 200 also includes GPS 234 for providing location information. A display 236, a speaker 238 and a microphone 239 are also provided. The display 236 and the speaker 238 can be configured to communicate visual and audio messages respectively to the user such as, for example, power remaining, connectivity status, diagnosis information, cartridge ID, cartridge count, incorrect substance loaded, substance expired, substance contaminated, alerts, alarms, time, or any other beneficial information. The microphone 239 can be configured to allow oral input of commands to the device 200, for example, status inquiry, power on/power off, voice log, etc. In various embodiments, a medical device can include any combination of the communication devices described herein.

The sensor 240 is fluidly coupled to the cartridge 210 and configured to receive the substance from the cartridge 210 and analyze the substance (e.g., medication) to determine one or more physical or biochemical parameters of the substance such as, for example, turbidity, expiry status, presence of contaminants, or other harmful substances present in the substance. The sensor 240 can include a colorimetric sensor (e.g., fluorescence, bioluminescent or color producing sensor) which can produce an optical signal indicative of a value or level of the parameter. In such embodiments, the device 200 can include imaging or optical detection equipment communicably coupled to the processor 224 for interpreting the optical signal and transforming the signal into a digital or analog signal communicable to the processor 224.

In other embodiments, the sensor 240 can include an infrared sensor for analyzing the substance. In still another embodiment, the sensor 240 can include an electrochemical sensor configured to measure a redox current or voltage of the substance in the absence or presence of a catalyst (e.g., a natural or synthetic enzyme, a precious metal, etc.) which corresponds to the parameter of the substance. In another embodiment, the sensor 240 can include an impedance or conductance sensor or an electromagnetic sensor. In such embodiments, the sensor 240 can include biological recognition molecules (e.g., polyclonal antibodies, monoclonal antibodies, antibody fragments, DNA, RNA, aptamers, synthetic recognition molecules and the likes) configured to bind with one or more components of the substance. The binding can alter an electrical or magnetic characteristic (e.g., impedance, conductance, dipole moment) of the sensor which can be interpreted by the processor 224 to determine the parameter. In still another embodiment, the sensor 240 includes a nanopore sensor. In various embodiments, the cartridge 210 can also contain reagents other than the substance which are communicated to the sensor 240 along with the medication to participate in biochemical reactions on the sensor 240 for determining the at least one physical or biochemical parameter of the substance (e.g., if the substance has expired or is contaminated).

Figure 3:
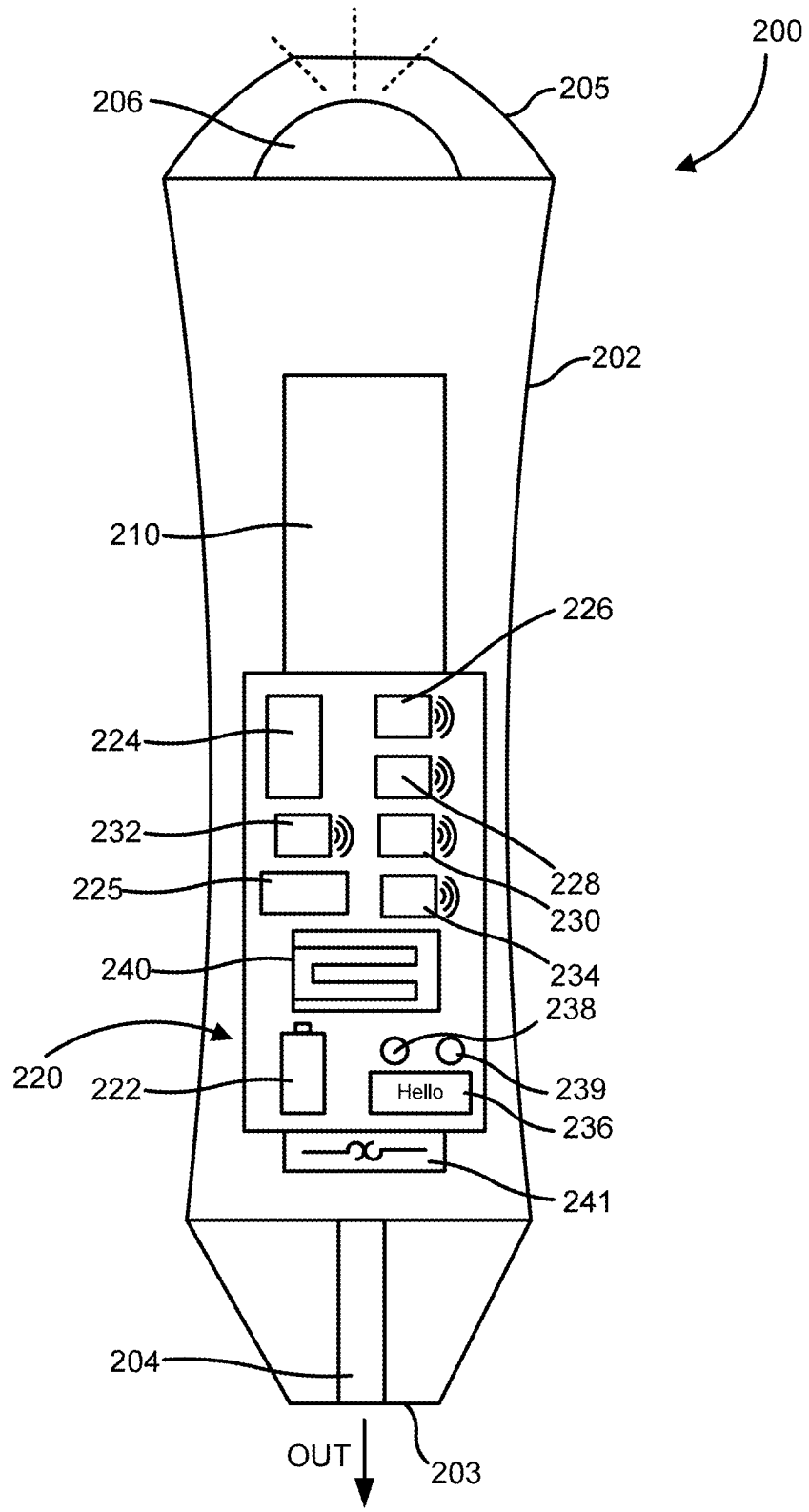
FIG. 3 is a front view of another configuration of the medical device of FIG. 2.

In various embodiments, the sensor 240 is removably coupled to the device 200 and can be disposable. Once a sensing operation has been performed, the used sensor 240 can be removed from the device 200 and a new sensor 240 inserted into the device to replace the old sensor 240. In other words, a fresh sensor 240 is used for each measurement. In other embodiments, the sensor 240 can be configured to perform a predetermined number of sensing or detecting operations with sufficient reliability before the sensor 240 has to be replaced with a fresh sensor 240. In various embodiments, the device 200 is configured to receive a variety of sensors such that each of the variety of sensors is configured to sense, detect or otherwise determine different physical or biochemical parameters of a substance or a bodily fluid inserted into the medical device. Expanding further, for example, the device 200 can be configured to receive a first sensor capable of measuring an expiry date of a medication contained within the device 200 or presence of harmful substance within the device 200. The device 200 can also be configured to receive a second sensor in addition to or in place of the first sensor which is configured to measure a first physical or biochemical parameter from a bodily fluid of a user (e.g., glucose). Furthermore, the device 200 can be configured to receive a third sensor in addition to or in place of the first sensor or the second sensor and so on. In this manner, the device 200 can be used to perform a variety of sensing operations simply by replacing an existing sensor 240 or including additional sensors 240 within the device 200. In various embodiments, the device 200 can be a vaporizer configured to vaporize the substance for oral communication to the user. For example, FIG. 3 shows another configuration of the device 200. In this configuration, the electronic circuitry 220 also includes a heater 241. The heater 241 is configured to vaporize the substance (e.g., a medication or any other substance described herein). The user can position the proximal end 203 of the housing 202 on the lips of the user and inhale to draw in the vapor. In particular embodiments, the substance includes a medication and the processor 224 can be configured to stop flow of the medication from the cartridge to the user once a predetermined quantity of the medication has been delivered to the user. Furthermore, a light source 206 (e.g., an LED) can be positioned on a distal end of the housing 202 and configured to emit light when the substance vapor is inhaled by the user. In other words, the device 200 can function as an e-cigarette. The distal end 205 can be transparent or translucent to allow light emitted by the light source 206 to be viewed from outside the housing 202.

Figure 4:
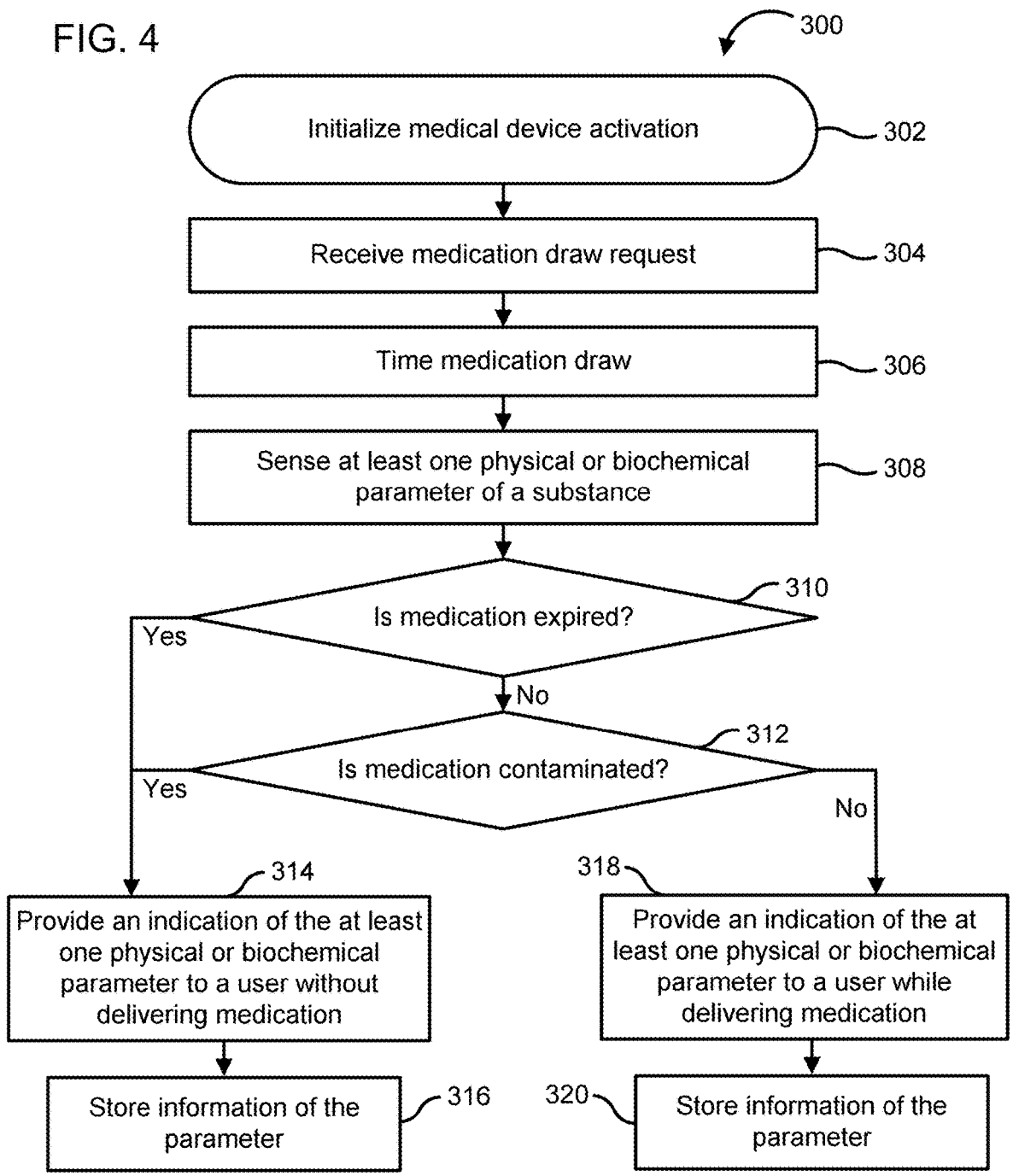
FIG. 4 is a schematic flow diagram of a method of operating the medical device of FIG. 2 or 3.

FIG. 4 is a schematic flow diagram of a method 300 for analyzing a medication contained within a medical diagnostic device, for example, any configuration of the device 200 or any other medical diagnostic device described herein. The method 300 includes initializing the medical device at 302, for example on, picking the device up, requesting a vapor draw, or inserting a new or different cartridge into the device. The device receives a medication draw request at 304. The medication draw request may be initiated by the user inputting a command into the device or inhaling into the proximal end (e.g., the proximal end 203 of the device 200 or 300). The medication draw request may include a predetermined duration based on a dosage to be delivered to the user. Such information can be stored in the memory 225. In various embodiments, the duration of the medication draw request may be unspecified and the time of the vapor draw may be measured at 306, for example, via a counter that can be included in the device. In still other embodiments, the medication draw request can activate the heater 241 of the device 200 to vaporize the medication before delivery.

At least one physical or biochemical parameter of the substance is sensed, at 308, for example, using the sensor 240 to determine an expiry date or presence of contaminants in the substance. The sensing can include any of the sensing methodologies described herein which yield a signal (e.g., current, voltage, impedance, resistance, or optical signal) which is communicated to the processor in the form of a digital or analog signal. It is determined if the medication is expired, at 310. For example, the processor 224 interprets the signals generated by the sensor 240 to determine if the medication has expired, as described before herein. If the medication is expired, the method proceeds to operation 314, and the user is provided an indication (e.g., an audio/visual signal, a Bluetooth®, Wi-Fi, RFID or cellular communication on a smartphone, tablet) of the parameter, without delivering the medication to the user. The user is thus informed that the medication is not safe for consumption. The information of the parameter is stored on the parameter at 316, for example, on the memory 225 or a storage medium of an external device such as a smartphone, tablet, computer or remote server. If the medication is not expired, the method detects if the medication is contaminated at 312. For example, the memory 225 can store instructions which are executed by the processor 224 to analyze the at least one physical or biochemical parameter to determine if the medication is expired and/or contaminated. If the medication is contaminated, the method 300 proceeds to operation 314.

If it is determined, for example, by the processor 224 that the medication is not expired and is free of contaminants, the method proceeds to operation 318 in which an indication of the parameter is provided to the user while delivering the medication to the user. The information of the parameter is stored at 320, for example, on the memory 225.

Figure 5:
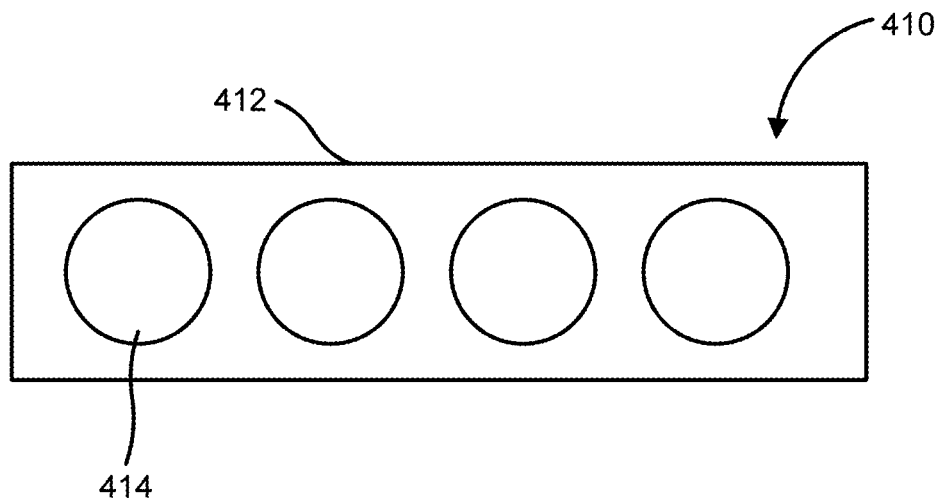
FIGS. 5 and 6 are illustrations of embodiments of a cartridge that can be included in the medical device of FIG. 2 or 3.

In various embodiments, a substance cartridge included in medical diagnostic device can include a plurality of medications. FIG. 5 is a front view of a cartridge 410 that can be included in the medical device 200 or any other medical device described herein. The cartridge includes a housing 412 and a plurality of silos 414 defined within the housing 412. Each silo 414 is filled or Tillable with the same substance or different substances (e.g., different medications corresponding to a health management regimen of a user). The silos 414 are defined along a longitudinal axis of the cartridge 410. The cartridge 410 is configured to be slidably repositioned within the device 200 or any other medical device herein and moved laterally along the longitudinal axis to position any one of the silos 414 in fluidic communication with the channel 204 or the heater 241, so that the substance present within the a particular silo 414 is delivered to the user via the channel 204. The repositioning can be performed manually, or using a linear actuator (e.g., a lead screw or a plunger).

Figure 6:
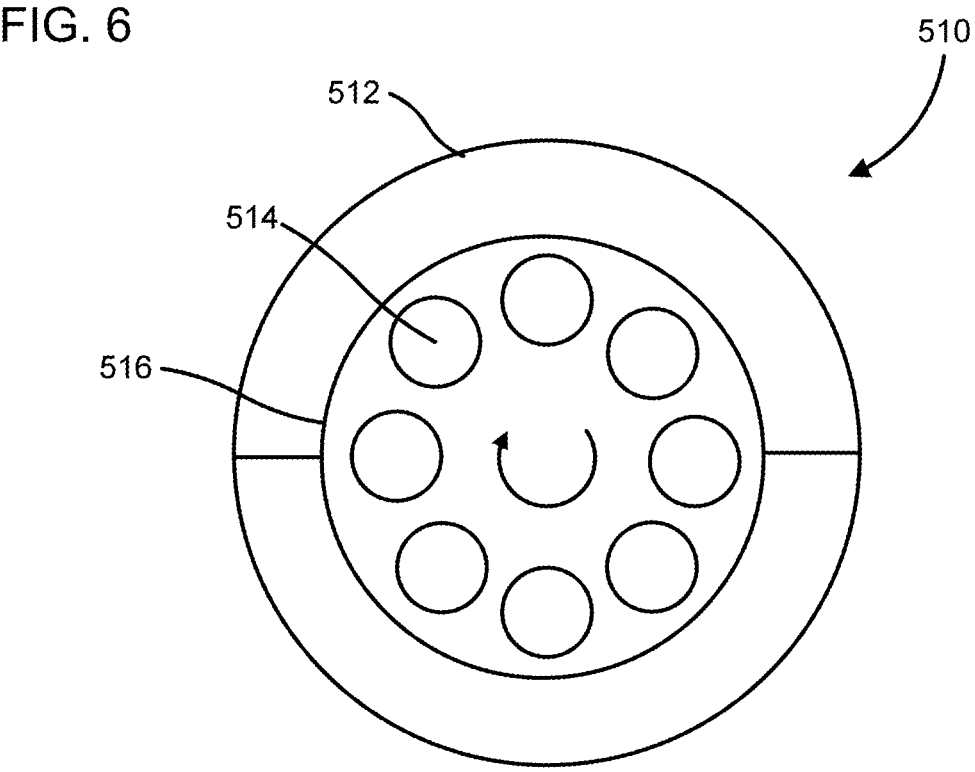

FIG. 6 shows another embodiment of a cartridge 510. The cartridge 510 includes a circular housing 512 with a plurality of substance silos 514 positioned radially about a central axis of the cartridge 510. The cartridge 510 can be rotatably repositioned within the device 200, for example manually, or by an actuator 516, such as a servo motor which can be coupled to the cartridge 510.

Any of the cartridges 410 or 510 may be programed with identifying information that indicates what substances are in the cartridge and what silo position the substance is positioned at accordingly. The silos 414 or 514 may each have a unique position identifier and each cartridge may have a silo quantity identifier indicating the number and/or position of each silo. The information may be stored in a memory device of the cartridge 410, 510 and may be communicably retrieved or sent to the actuator to control the position of the cartridge in accordance with a user selection.

In particular embodiments, when cartridge 510 rotates, as discussed further herein, it is possible for one sub-cartridge (e.g. silo 512) to have the substance contained therein vaporized at a certain wattage/voltage, while a different sub-cartridge, for example containing a different substance, may be vaporized at a different wattage/voltage. Additionally one sub-cartridge might just dispense (and not vaporize) a substance (pill, powder, liquid, gel) or any combination of the above.

In particular embodiments each of the cartridges 410, 510 and the silos 414, 514, for example a cartridge containing weed, wax, or shatter, operates in a manner similar to an oven. In particular embodiments containing a liquid each of the cartridges 410, 510 and/or the silos 414, 514 use a wick/coil system. In particular embodiments the cartridges 410, 510 and/or the silos 414, 514 may use one or more of an ultrasonic diffuser, a cold air diffuser, an evaporative diffuser, or a heat diffuser. The ultrasonic diffuser uses electronic frequencies to create vibrations that are carried to the surface where oils are floating. The vibrations from the ultrasonic diffuser vaporize the oil and disperse it into the air without using any kind of heat. The cold air diffuser uses room-temperature air to blow the oil into a nebulizer where it is vaporized. The cold air diffuser can diffuse quickly and efficiently. The evaporative diffuser includes a fan that blows air through a pad or filter where the oil sits and vaporizes the oil on the pad. The heat diffuser uses a heat source to disperse the essential oil. In example embodiments, the cartridge 410, 510 may remain stationary and the actuator may reposition the heater for heating the silo 414,514 and/or may reposition an output port to release the vaporized substance.

Figure 7:
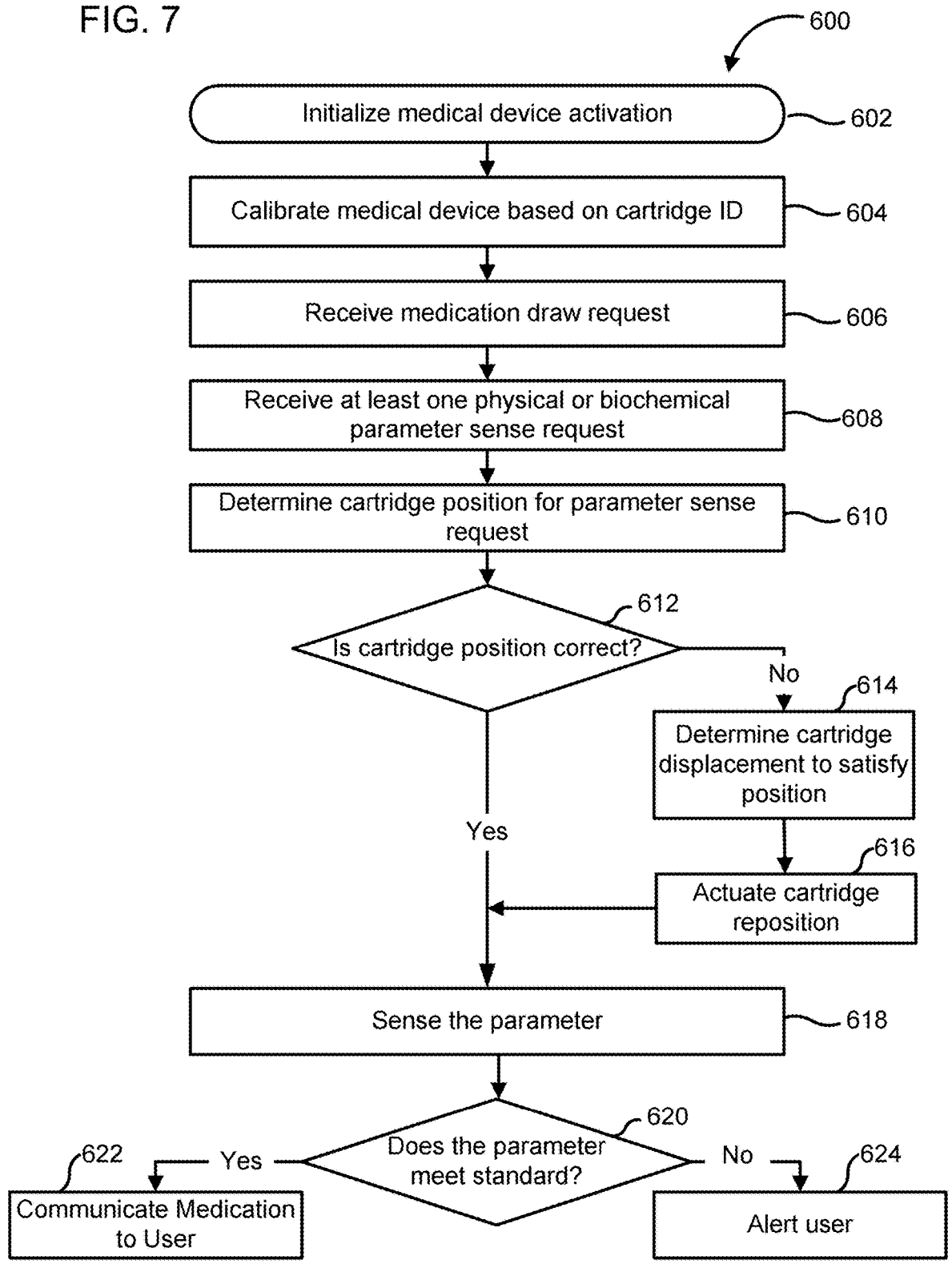
FIG. 7 is a schematic flow diagram of a method of operating a medical diagnostic device that includes the cartridge of FIG. 5 or 6.

FIG. 7 is a schematic flow diagram of an exemplary method 600 for repositioning a cartridge of a medical diagnostic device for delivering a predetermined medication to a user and sense one or more physical or biochemical parameters of the medication to determine if the medication is fit to be consumed by the user. The method includes initializing medical device activation at 602, for example in response to a user turning the apparatus 200 on, picking the device up, requesting a vapor draw, or inserting a new or different cartridge 410 or 510. The medical diagnostic device 200 is calibrated based on a cartridge ID at 604, which is inserted in to the device and the information provided by the cartridge 410 or 510 regarding the device silos 414 or 514, the number of silos, the position of the silos, and the contents of the silos.

The device receives a medication draw request at 606, which can include a vapor draw request. In some embodiments, the vapor draw request may include an indication of which one or more substance to inhale at a time. If, for example, a cartridge is loaded with two substances that should not be simultaneously mixed, the medical diagnostic device may deny the request. If the request is approved, the device receives an at least one physical or biochemical parameter sense request at 608, to sense the parameter of the medication. The parameter sense request can be for a single medication included in one silo 414 or 514 of the cartridges 410 or 510, whichever is included in the medication device 200, or more than one medications stored in the plurality of silos of the device 200.

A cartridge position for the parameter sense request is determined at 610. The cartridge position corresponding to the parameter sense request can stored in the memory 225 and interpreted by the processor based on cartridge ID information provided to the device 200 when the cartridge is loaded on the device 200. In other embodiments, for example, when the cartridge 410 or 510 are refillable with custom medications, the information can be manually provided by the user, for example, entered in an app on a smartphone which is synced with the device 200 via a hardwired, Bluetooth® or Wi-Fi connection.

It is determined if the cartridge position is correct at 612, i.e., is at least one of the silo 414, 514 including the medication for which the draw request and sense request was obtained in fluid communication with the vaporizer 241 or the channel 204 of the device 200. If an incorrect silo 414 or 514 is aligned, a cartridge displacement sufficient to satisfy position is determined at 614, and a cartridge reposition is actuated at 616. The cartridge repositioning can include slidably displacing the cartridge (e.g., the cartridge 410) or revolving the cartridge (e.g., the cartridge 510) manually or using an actuator (e.g., a linear actuator or a servo motor). Once the cartridge is repositioned, or the cartridge was correctly positioned at operation 612, the parameter is sensed at 618, for example to determine if the medication has expired or is contaminated. At 620, it is determined if the parameter meets a predetermined standard. If the medication meets the standard, the medication is communicated to the user at 622. If the medication fails the standard, for example is expired or contaminated, the user is alerted at 612 and the medication is not communicated to the user.

Figure 8:
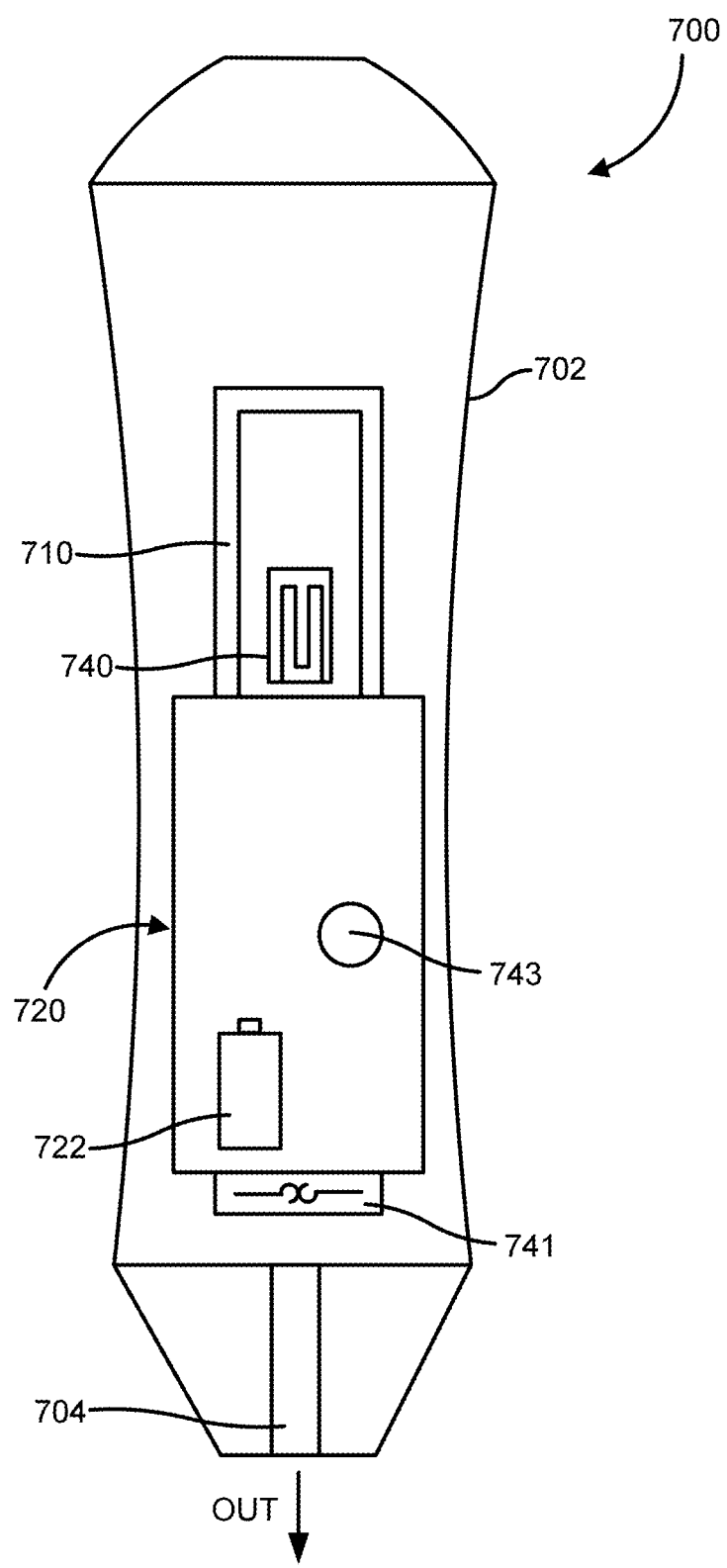
FIG. 8 is a front view of a medical diagnostic device according to another embodiment.

In particular embodiments, a sensor can be positioned within a cartridge of a medical diagnostic device. FIG. 8 is a front view of medical diagnostic device 700 according to another embodiment. The device 700 includes a housing 702 defining a channel 704 at a proximal end of the housing 702 to deliver a substance, for example, any of the substances described herein to a user. The housing 702 can be substantially similar to the housing 202 described herein and therefore not described in further detail herein.

A substance cartridge 710 is positioned within the internal volume of the housing 702. The cartridge 710 can include the cartridge 210, 410, 510 or any other cartridge described herein are configured to include one or more substances (e.g., any of the substances described herein) within one or more silos of the cartridge 710. Electronic circuitry 720 is positioned within the internal volume of the housing 702 and includes a power source 722 and a heater 741. The electronic circuitry 720 can be substantially similar to the electronic circuitry 220 described herein and can include one or more components described with respect to the electronic circuitry 220, excluding the sensor 240. Instead, a sensor 740 is embedded within the cartridge, for example, embedded within one or more silos included in the cartridge. The sensor 740 can include a dipstick type sensor (e.g., a lateral flow sensor, a paper microfluidic sensor, microfluidic sensor including a plurality of sensors or any sensor as described with respect to the sensor 240 described before herein). The sensor 740 can be configured to measure one or more physical or biochemical parameters of a substance (e.g., medication) contained within the cartridge 710 as described before herein. The sensor 740 can be disposable so that each time a new sensor 740 is inserted into the device 700 each time a new cartridge 710 is coupled to the device 700. In some embodiments, insertion of the cartridge 710 into the device 700 brings the sensor 740 in electrical communication with the electronic circuitry 720, for example via magnetic electrical couplers, snap couplers or contact couplers. In some embodiments, the cartridge can be configured to include one or more sensors that are replaceable. As such, even if the cartridge still has medication remaining in one or more silos and does not need to be replaced, a user can replace one or more sensors of the cartridge without having to replace the cartridge itself.

In some embodiments, the sensor 740 can also be configured to measure a level of liquid substance remaining in the cartridge 710. For example, the sensor 74 can include a grid or matrix type sensor configured to measure a remaining vaporizable substance in the cartridge 710 regardless of the physical orientation of the device 700 (e.g., held vertically, horizontally or therebetween). For example, the control system 720 may include a processor (e.g., the processor 224) which may be to determine quantity of a cartridge based on usage history and parameters. For example, vapor or aerosol test may be run on cartridge 710 to determine a level of substance remaining within the cartridge 710. The cartridge 710 may include the information in the on-board memory (e.g., the memory 725) or the information may be pre-programmed into the processor. The aerosol test may be based on the fully charged power source 722, and a filled cartridge 710, test different input signals (e.g., current or voltages), and determine how much power vaporizes how much of the given vaporizable or dispensable product from the cartridge 710 based on a typical vapor draw, corresponding battery power reduction in relation to the total quantity of a remaining dispensable substance. This information may be programmed into the cartridge 710 or in the processor. The aerosol test is advantageous because it permits a system that functions without additional hardware, pressure sensors, fluid monitoring, etc. which might be used in various implementations to determine the remaining dispensable substance in a device or cartridge. The aerosol test also has the advantage of permitting measuring the remaining substance without requiring the device 700 to be held in a particular orientation to accurately gauge the remaining substance. This test permits the measurement to be completed with an insert in the tank in a grid like format so that a mathematical algorithm may be run to determine the remaining volume irrespective of the orientation of the device 700.

The processor (e.g., the processor 224) uses this information based on the actual inhalation of the user, to accurately update and monitor the burn rate of a specific user to accurately replenish the supply for the user on time as discussed further herein. For example, the electronic circuitry 720 can include a counter or timer 743 to determine a quantity, such as time of vaporization or duration of inhalation. In particular embodiments, the electronic circuitry 720 may be configured to monitor the duration of vaporization, for example, by determining the duration and quantity of heating events by heater 741 configured to heat the substance in the cartridge 710 for vaporization of the substance.

Figure 9:
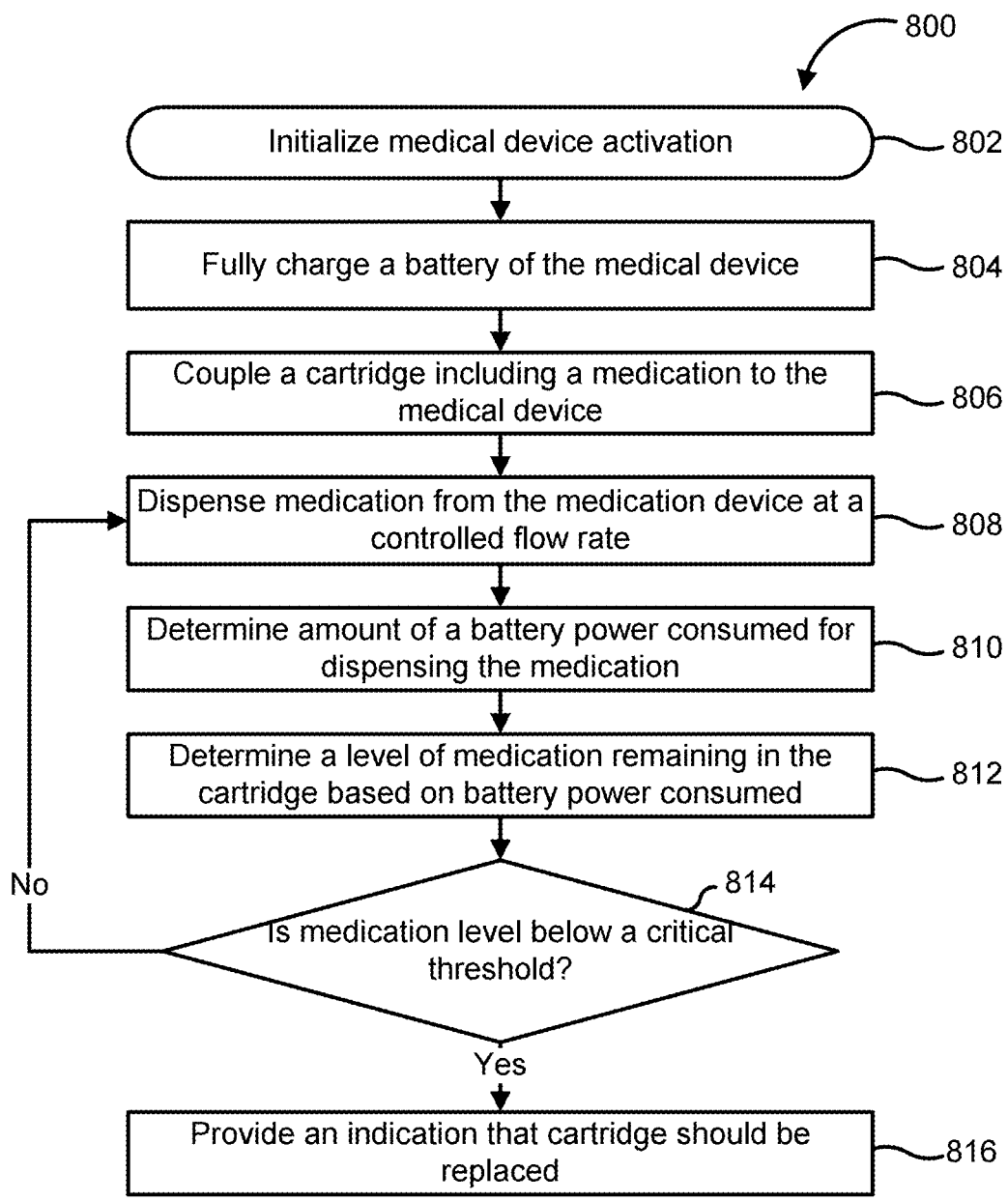
FIG. 9 is a schematic flow diagram of a method for determining a level of medication contained within a medication diagnostic device.

FIG. 9 is a schematic flow diagram of an exemplary method 800 for determining a level of medication or any other substance remaining in a cartridge of a device, for example the cartridge 710 of the device 700. The method 800 includes initializing the medical diagnostic device activation at 802, for example in response to a user turning the apparatus 700 on, picking the device up, requesting a vapor draw, or inserting a new or different cartridge 710. The battery of the device is fully charged at 804, for example, the power source 722 of the device 700 is coupled to an outlet power to charge the power source 722, or a new or freshly charged power source is inserted into the medical device 700.

A cartridge including a medication is coupled to the medical device 806. The medication is dispensed at a controlled flow rate from the medical device 808. For example, the medication is vaporized by the heater 741 and includes valves, constructions or capillary flow channels to allow the medication to be delivered to the user at controlled flow rate irrespective of the inhalation or otherwise draw pressure exerted by the user on the channel 704. In other embodiments, the flow rate can vary but is normalized via a pressure measurement component. For example, the device (e.g., the device 700) can also include a pressure sensor. Data from the pressure sensor can be used to normalize the actual flow rate to obtain a normalized flow rate which is used to determine the level of the medication remaining in the cartridge 710.

The amount of battery power consumed is determined at 810. The amount of battery power remaining can be determined from a known power of the battery 722 when fully charged and measured power of the battery 722 after the dispensing or drawing medication from the device 700. In other embodiments, the battery power consumed can be measured in real time and is based on the amount of power required to operate the heater 741 for a given flow rate or predetermined flow rate of the dispensed medication. In still other embodiments, data from the timer or counter 743 corresponding to the dispensing or drawing time of the medication is correlated to the amount of battery 722 power consumed.

The level of medication remaining in the cartridge is determined based on battery power consumed at 812. For example, as described before, the processor (e.g., the processor 224) uses lookup tables or algorithms stored therein or in an onboard memory (e.g., the memory 225) to determine an amount of medication or medication vapor consumed during the dispensing operation 808. The amount of medication consumed is then subtracted from the original amount of medication contained within the cartridge 710 to obtain the amount of medication remaining. The remaining level is now used as the baseline level for subtracting an amount of medication dispensed in a subsequent dispensing operation to determine a new level remaining of the medication, and so on. Once the level of medication remaining is determined, the method 800 determines if the medication level is below a critical threshold at 814. The critical threshold level can be stored on the processor or memory and can, for example, correspond to less than 10%, less than 5%, or less than 1% of the original volume of the medication remaining in the cartridge 710. In various embodiments, the critical threshold can be determined, for example, based on a type of substance, a dosage of the substance to be delivered, an actual or expected usage of the substance, the manufacturing or expiry date of the substance, the number of dosages of the substance that have already been delivered or any other suitable parameter. In particular embodiments, the critical threshold can dynamically change or vary based on various parameters such as, for example, time of day, manufacturing or expiry date, time the cartridge 710 has been loaded into the device 700, next scheduled refill pick up date, a predetermined time interval defined by the user or a medical provider (e.g., a doctor, a nurse or a pharmacist), etc. In various embodiments, once the substance level is at or below the critical level, the device 700 can be configured to inform a medical provider (e.g., a caregiver, a doctor, a nurse, or a pharmacy) that a refill of the substance is due or order a refill of the cartridge 710. Such a communication can be performed using any of the communication devices that can be included in the electronic circuitry 720 (e.g., a Bluetooth®, or Wi-Fi communication to a smartphone, tablet or communication app which is further communicated to the medical providers server, or a direct communication to the medical providers server, for example, via the internet). If the level of medication remaining is above the critical threshold, the method 800 returns to operation 808 and operations 808 to 814 are repeated until the level of medication drops below the critical level or a user turns the device 700 off. If the level of medication drops below the critical level, the device provides an indication to the user that the cartridge should be replaced at 816 (e.g., via an audio/visual alert, an SMS message, message to an app on a smartphone, tablet or computer in communication with the device 700).

Figure 10:
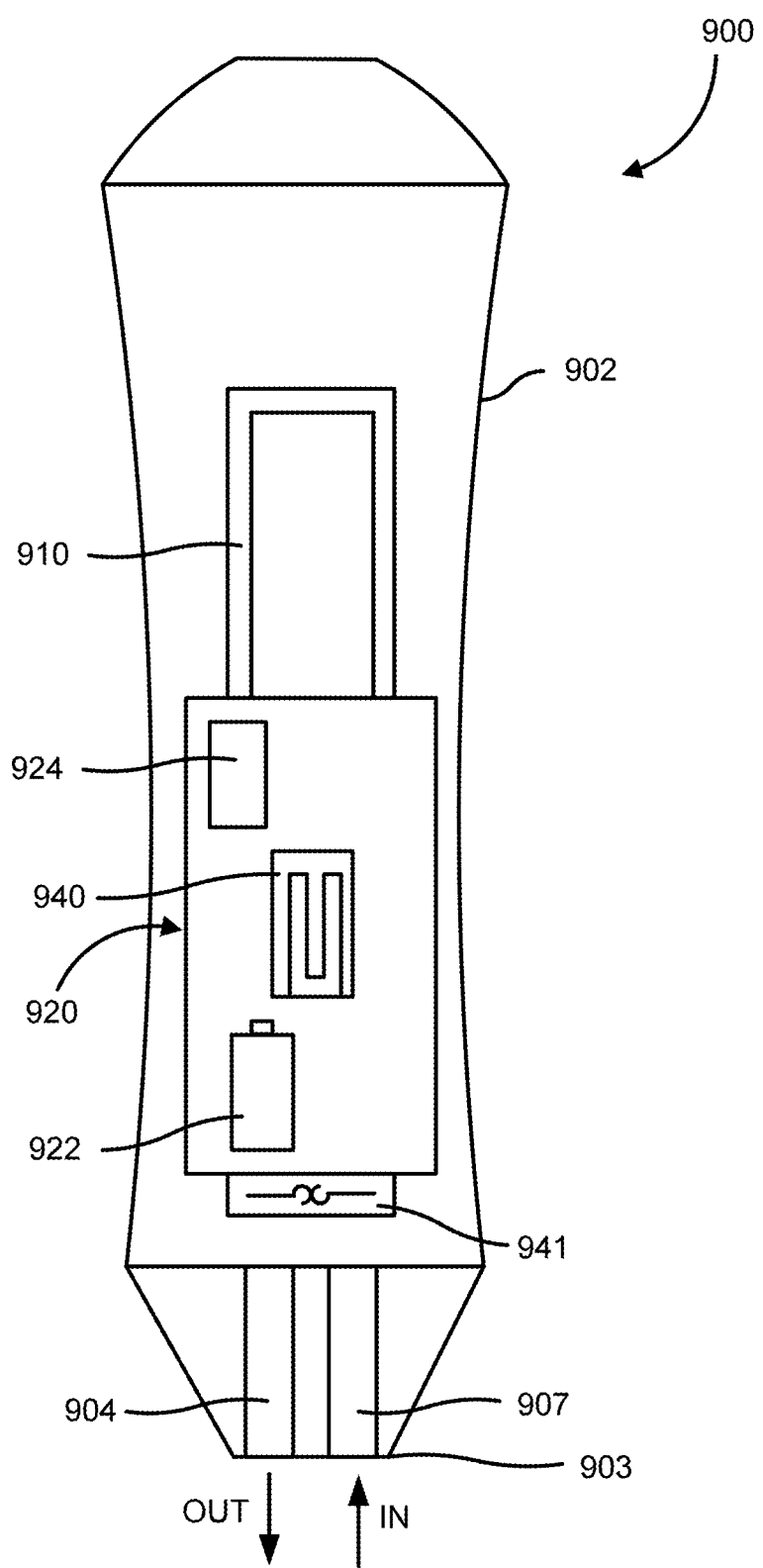
FIG. 10 is a front view an embodiment of a medical diagnostic device for analyzing a breath or saliva of a user and delivering a substance to the user based on the sensing.

In some embodiments, any of the medical devices described herein can be used to sense one or more physical or biochemical parameters of included in a breath or saliva of a user and deliver one or more substance to the user based on the physical parameter. For example, FIG. 10 is a front view of a medical diagnostic and delivery device 900. The device 900 includes a housing 902 defining an internal volume. An inlet channel 907 is defined on a proximal end 903 of the housing 902. The proximal end 903 is configured to be engaged by a user, for example positioned on the lips of the user such that the user can deliver a breath into the inlet channel 907 or insert saliva into the inlet channel 907. In particular embodiments, the inlet channel 907 includes a capillary so that the saliva can be communicated via capillary action to a sensor 940 of the device 900. In other embodiments, a lateral flow strip can be embedded in the inlet channel 907 configured to communicate saliva to the sensor 940 via wicking action. It still other embodiments, a micro-vacuum pump (not shown) can be in fluidic communication with the inlet channel 907 to draw in the saliva and deliver the saliva to the sensor 940.

The housing 902 also defines an outlet channel 904 in fluidic communication with a substance cartridge 910 and/or the heater 941 positioned within the internal volume of the housing 902. The outlet channel 904 is configured to deliver the substance contained within the cartridge to the user, for example, a liquid substance, powdered substance, substance mist, substance aerosol, or substance vapor to the user. In some embodiments, a one way valve can be positioned within the outlet channel 907 to allow breath or saliva to only flow into the device 900. Similarly, a one way valve can also be positioned within the outlet channel 904 to allow the substance to only flow out of the outlet channel 904 towards the user.

The substance cartridge 910 is positioned within the internal volume and contains one or more substances positioned within the cartridge 910. In some embodiments, the cartridge 910 can be a repositionable cartridge configured to include a plurality of substances therewithin such as, for example, the cartridge 410 or 510 described before herein. The substance can include, for example, caffeine, panax, ginseng, gingko, biloba, bitter orage, cola-nut, guarana, natrum carbonicum, green tea, cocoa extract, cannabis, yerba mate, other vaporizable or inhalable supplements, pharmaceuticals, medicines, waxes, liquids, a breath alcohol masking agent, or any other substance which can be delivered to the user. The substance cartridge 910 is in fluidic communication with at least one of the heater 941 (e.g., to allow vapor to be produced which is communicated to the user via the outlet channel) and the outlet channel 904 (e.g., to allow liquid substance, powder, a mist or aerosol to directly delivered to the user).

The device 900 includes electronic circuitry 920 that includes a battery 922, a processor 924, the sensor 940 and the heater 941. While not shown, the electronic circuitry 920 can include any other components, for example, the communication devices, as described with respect to the electronic circuitry 220. In some embodiments, the electronic circuitry 920 can be substantially similar to the electronic circuitry 220. The heater 941 is configured to vaporize the substance provided by the cartridge 910 to produce vapors which are communicated to the user. Furthermore, the sensor is in fluidic communication with the inlet channel 907 and configured to receive the breath or saliva of the user.

As described before, the device 900 is configured to detect one or more physical or biochemical parameter of the user by analyzing a breath or saliva of the user. The user can blow into the inlet channel 907 or communicate saliva into the inlet channel 907 which is communicated to the sensor 940. The sensor 940 can be substantially similar to the sensor 240 described before or 740 before herein and configured to determine one or more physical parameters of the user such as, for example, glucose level, blood alcohol level (BAC), THC level (biomarker for marijuana), adrenal conditions (e.g., Cushing's disease, Addison's disease), hormone levels, altered female hormone states (e.g., PCOS, menopause, anovulation, pregnancy, irregular period cycles), altered male hormone states (e.g., hypogonadism, andropause, hyperestrogenic states), metabolic disorders (e.g., insulin resistance, diabetes, muscular dystrophy) benign and metastatic neoplasms (e.g., breast cancer, pancreatic cancer, prostate cancer, oral cancer, lung and throat cancer, etc.), infection diseases (e.g., HIV, viral hepatitis, flu, H1N1 flu, SARS virus, amoebiasis, heliobacter pylori infections, C. difficius infections, strep throat), food allergy, cortisol levels as indicators of stress, progesterone, or any other disease or medical condition for a which a biomarker is expressed in the breath or saliva of the user. While shown as included in the electronic circuitry 920, in particular embodiments, the sensor can be included in the cartridge 910, as described before with respect to the cartridge 710 included in the medical diagnostic device 700.

The processor 924 can be to receive signals from the sensor 940 and determine the medical condition presented by the user, for example, using instruction such as look up tables, algorithms or calibration curves stored on the processor 924 or on on-board memory (e.g., the memory 225 described before herein). Based on the diagnosis the processor 924 can be further configured to identify at least one medication contained within the cartridge 910 which is to be delivered to the user to address the medical diagnosis. For example, in one instance the diagnosis can be high glucose and the processor 924 identifies that insulin contained within the cartridge 910 is to be delivered to the user. In another instance, the processor 924 identifies that a blood alcohol level (BAC) of the user is high and identifies a BAC masking substance contained within the cartridge 910 is to be delivered to the user. The cartridge 910 can include a positionable cartridge (e.g., the cartridge 410 or 510) including a plurality of substances (e.g., medications) targeting a plurality of medical conditions, for example, any of the medical conditions described herein. Based on the diagnosis performed by the processor 924 based on the parameter sensed by the sensor 940, the processor 924 can command an actuator (e.g., a linear actuator, a lead screw, a plunger or a servo motor) to reposition the cartridge 910 such that the identified substance which is to be delivered to the user is in fluidic communication with the outlet channel 904 and the heater 941. In particular embodiments, the cartridge 910 can be manually repositionable. In such embodiments, the processor 924 can send a command to a communication system (e.g., a display, an audible alarm via a speaker, or communicate to an app on smartphone, tablet or computer via Bluetooth®, Wi-Fi, cellular network, RFID or the likes) to indicate to the user the correct position of the cartridge 910. The user can then manually reposition the cartridge 910 to bring the identified substance in fluidic communication with at least one of the outlet channel 904 and the heater 941.

Figure 11:
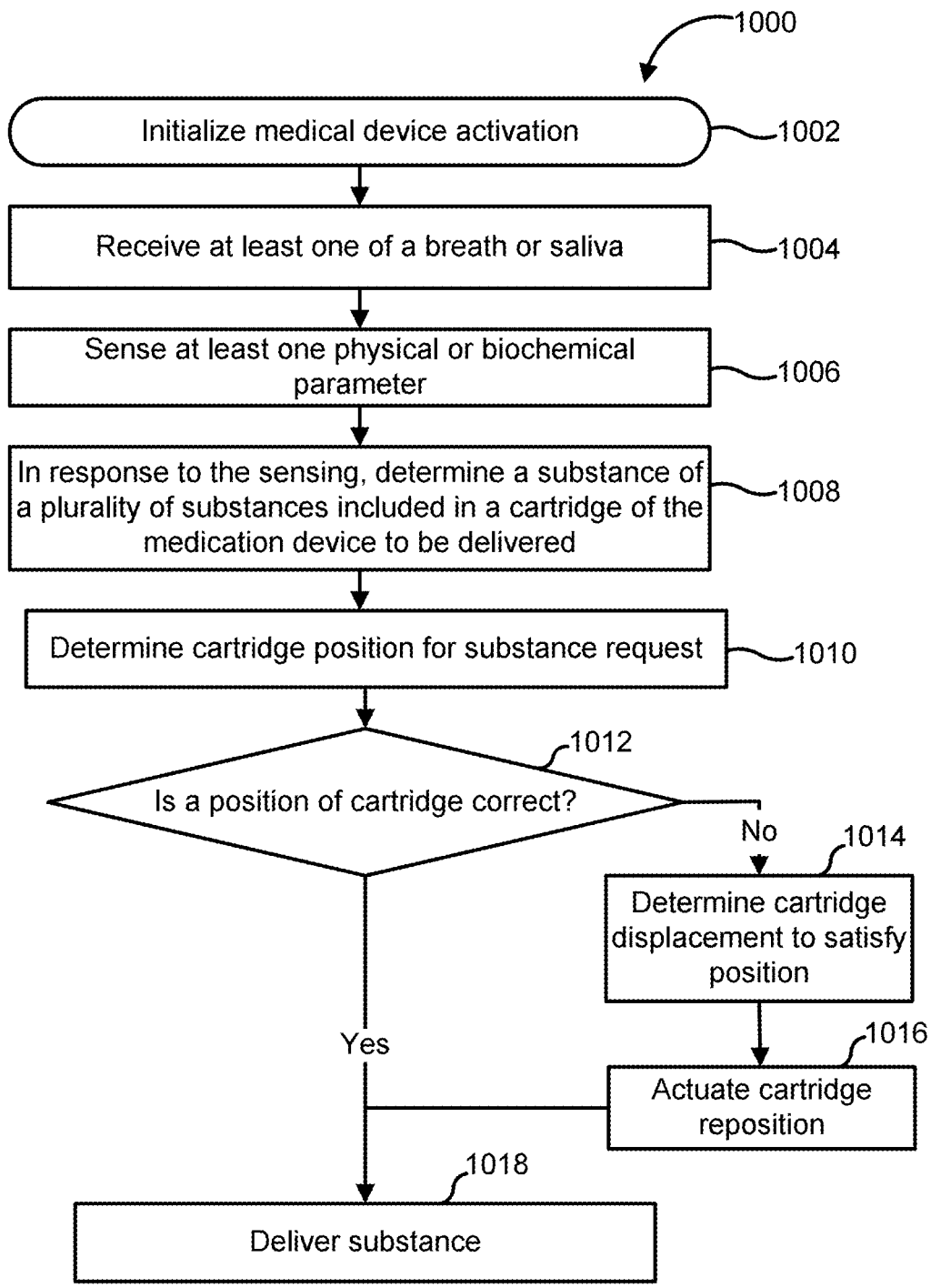
FIG. 11 is a schematic flow diagram of a method for sensing at least one physical or biochemical parameter from a breath or saliva of a user to diagnose a medical condition and deliver a substance to a user based on the diagnosis.

FIG. 11 is a schematic flow diagram of a method 1000 for sensing at least one physical or biochemical parameter of breath or saliva of a user to diagnose a medical condition and deliver at least one medication to the user to address the medical condition using a medical diagnostic and delivery device (e.g., the device 900 or any other medical diagnostic and delivery device described herein).

The method 1000 includes initializing a medical device activation at 1002, for example in response to a user turning the apparatus 900 on, picking the device up, requesting a vapor draw, or inserting a new or different cartridge 910. At least one of breath or saliva is received at 1004. For example, the user can blow into the inlet channel 907 of the medical device 900 or spit into the inlet channel 907. At least one physical or biochemical parameter is sensed at 1006. The breath or the saliva is communicated through the inlet channel 907 to the sensor 940 of the device 900, which senses at least one physical or chemical parameter included in the breath or saliva, as described before herein.

In response to the sensing, at least one substance of a plurality of substances included in the cartridge of the medical diagnostic and delivery device which is to be delivered is determined at 1008. For example, the processor 924 interprets signals (e.g., current, voltage, optical signals) received from the sensor to determine a medical condition of the user, for example, a high glucose level or high BAC. Based on the diagnosis the processor 924 determines an appropriate substance among the plurality of substances included in the cartridge 910 to be delivered to the user (e.g., insulin to lower blood glucose, BAC masking agent, Tylenol®, ibuprofen, anti-viral, anti-bacterial, anti-vomiting, anti-diarrhea, etc.). A cartridge position for substance delivery request is determined at 1010. For example, the processor 924 determines the position of a silo included in a plurality of silos of the cartridge 910 that includes the medication identified to be delivered to the user.

It is determined if the cartridge position is correct at 1012. For example, the processor 924 determines if a silo of the cartridge 910 included in a plurality of silos of the cartridge 910 that includes the substance that is to be delivered to the user is in a designated position to allow delivery to the user. If the cartridge position is correct, the substance is delivered to the user 1018. If the position of the cartridge is incorrect, a cartridge displacement to satisfy position is determined at 1014. A cartridge repositioned is then actuated, at 1016, for example, by a command from the processor 924 to a linear actuator or a servo motor to reposition the cartridge 910, as described before herein. Once the cartridge 910 is repositioned, the methods proceeds to 1018 and the substance is delivered to the user.

Figure 12:
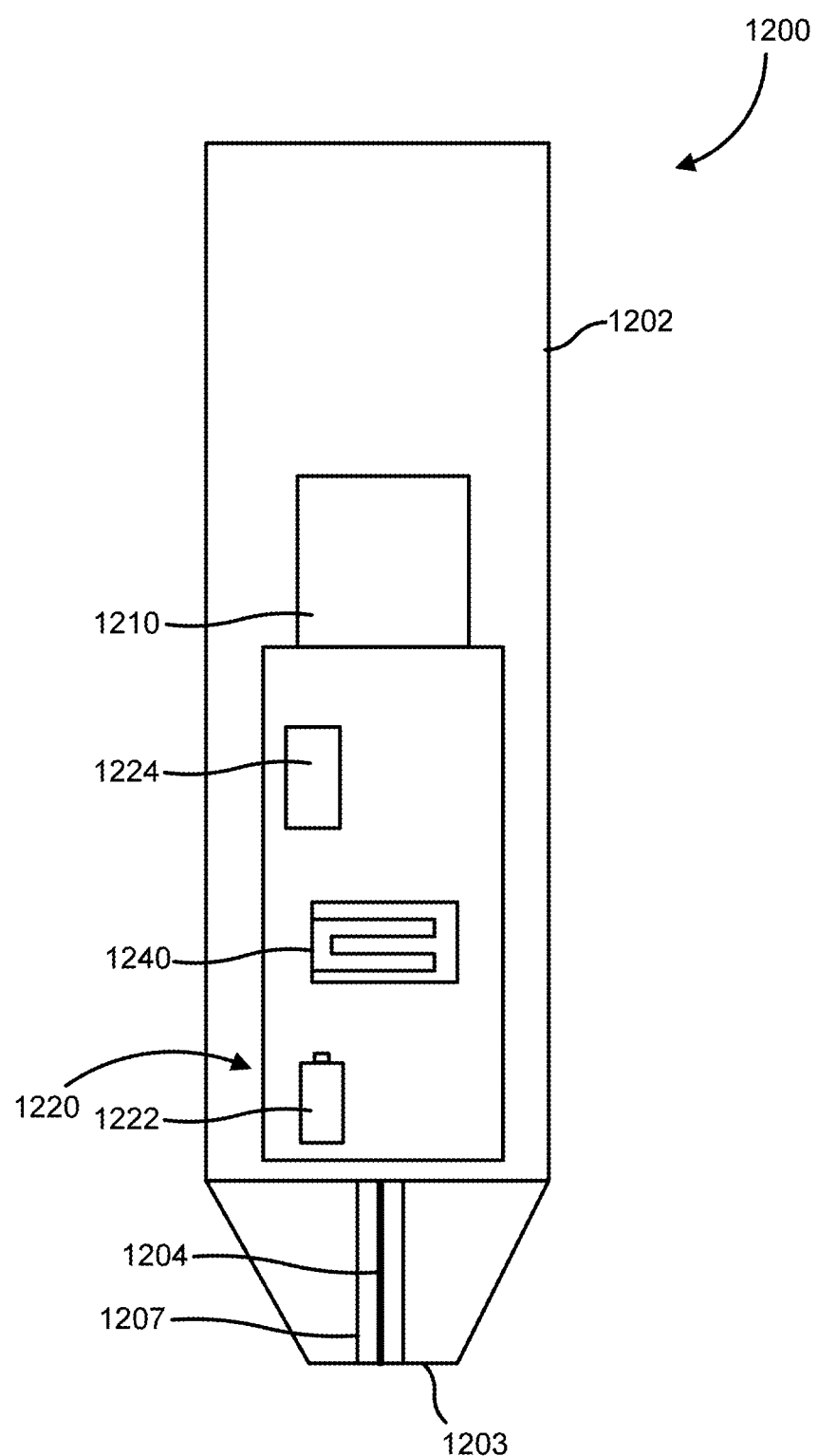
FIG. 12 is a front view of another medical diagnostic device for measuring a temperature and sensing a physical or biochemical parameter included in the saliva of a user.

In some embodiments, a medical diagnostic device can be configured to measure a temperature of a user and simultaneously measure one or more physical or biochemical parameters from saliva of a user. In other words, in some embodiments, medical diagnostic device can have a form factor and perform the functions of a conventional thermometer while also monitoring various physical and/or biochemical parameters of the user. For example, FIG. 12 is a front view of another embodiment of a medical diagnostic device 1200 for measuring a temperature and one or more physical or biochemical parameters of a user.

The device 1200 includes a housing 1202 defining an internal volume. A temperature sensor 1204, for example, a thermocouple, a thermistor, a mercury column or an alcohol column is positioned at a proximal end 1203 of the housing 1202. A user can position the proximal end of the device 1200 in a buccal cavity of the user so that the temperature sensor 1204 senses the temperature inside the buccal cavity of the user representative of a core body temperature of the user. A fluidic channel 1207 is also defined on the proximal end of the housing 1202 and configured to receive saliva of the user from within the buccal cavity of the user while the user measures the temperature of the user. The fluidic channel 1207 is configured to communicate the saliva to sensor 1240 include in an electronic circuitry 1220 of the device 1200. In some embodiments, the fluidic channel 1207 includes a capillary channel configured to draw saliva into the fluidic channel 1207 via capillary action. In other embodiments, a lateral flow strip can be positioned in the fluidic channel 1207 to draw saliva and communicate saliva to the sensor 1240 via capillary action. In various embodiments, the fluidic channel 1207 is defined around the temperature sensor 1204 as shown in FIG. 12 so at least a portion of the temperature sensor 1204 is positioned within the fluidic channel 1207. In other embodiments, the fluidic channel 1207 can be positioned adjacent to the temperature sensor 1204.

The electronic circuitry 1220 includes a battery 1222, a processor 1224, and a sensor 1240. While not shown, the electronic circuitry 1220 can also include an on-board memory and various other components such as the communication devices described with respect to the electronic circuitry 220. In some embodiments, the electronic circuitry 1220 is substantially similar to the electronic circuitry 220 described herein. In some embodiments in which the temperature sensor 1204 includes a thermistor or a thermocouple, the processor 1224 can be specially preprogrammed to interpret signals from the temperature sensor 1204 to determine a temperature of the user. The sensor 1240 is configured to receive saliva via the fluidic channel 1207 and determine one or more physical and or biochemical parameters of the user from the saliva. Such parameters can include glucose level, BAC, adrenal conditions (e.g., Cushing's disease, Addison's disease), hormone levels, altered female hormone states (e.g., PCOS, menopause, anovulation, pregnancy, irregular period cycles), altered male hormone states (e.g., hypogonadism, andropause, hyperestrogenic states), metabolic disorders (e.g., insulin resistance, diabetes, muscular dystrophy) benign and metastatic neoplasms (e.g., breast cancer, pancreatic cancer, prostate cancer, oral cancer, lung and throat cancer, etc.), infection diseases (e.g., HIV, viral hepatitis, flu, H1N1 flu, SARS virus, amoebiasis, heliobacter pylori infections, C. difficius infections, strep throat), food allergy, cortisol levels as indicators of stress, progesterone, or any other disease or medical condition for a which a biomarker is expressed in the saliva of a patient. The sensor 1240 can be substantially similar to the sensor 240 described herein with respect to the device 200 and therefore not described in further detail herein.

In some embodiments, a cartridge 1210 is also included in the device 1200. The cartridge 1210 can be in fluidic communication with the sensor 1240. The cartridge 1210 can include one or more reagents which can be communicated to the sensor 1240 for participating in a biochemical reaction on the sensor involved in the sensing of a biochemical parameter of the saliva. In other embodiments, the cartridge can include a wash fluid to clean the sensor 1240 after a sensing operation has been performed.

Figure 13:
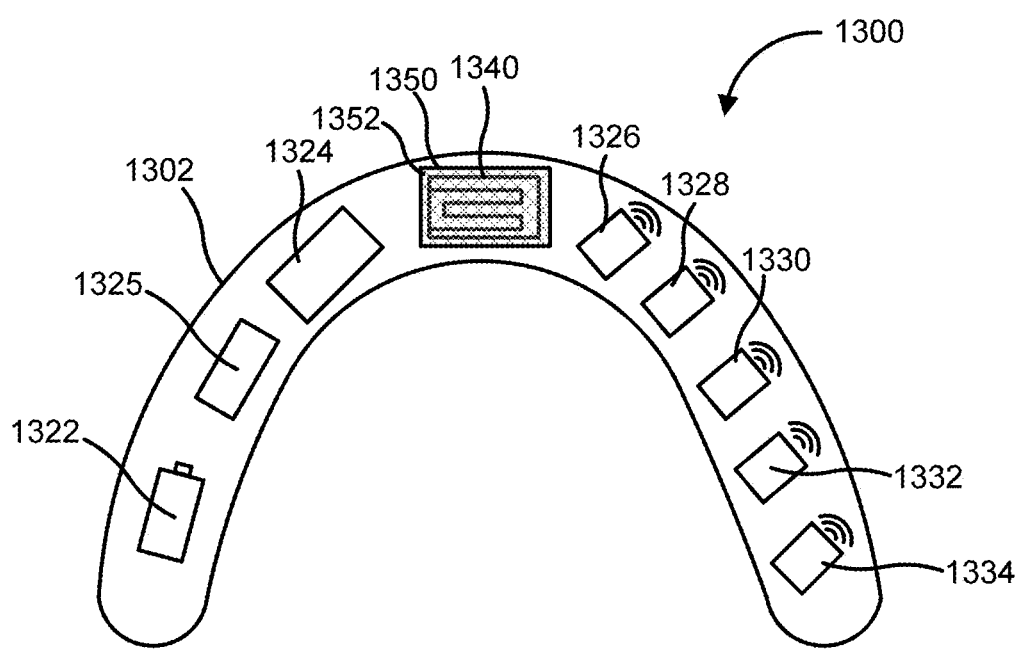
FIG. 13 is a front view of yet another medical diagnostic device configured to be positioned within a buccal cavity of a user and sense a physical or biochemical parameter included in the saliva of the user.

The device 1200 is configured to perform an on-demand diagnostic of health of a user based on one or more physical or biochemical parameters measured from the saliva of the user. In other embodiments, a medical diagnostic device can be configured to perform long-term diagnostics from the saliva of the user. For example, FIG. 13 shows a medical diagnostic device 1300 which includes a housing 1302 defining an internal volume. The housing 1302 has the form factor or otherwise shape of a dental retainer, dental brace or a mouth guard such that the device 1300 can be positioned within the buccal cavity of a user and retained within the buccal cavity of the user. For example, the housing 1302 can include a brace or clamps configured to clamp the teeth of the user and secure the housing around the teeth. In some embodiments, grooves, depressions or indents corresponding to the bite of the user can be defined on the housing 1302, which allow the housing 1302 to be removably positioned over the teeth of the user. For example, the user can position the housing 1302 of the device 1300 over a top or bottom row of teeth and leave the device thereon (e.g., overnight) to perform prolonged diagnostic on the saliva of the user.

The device 1300 includes a power source 1322, for example, a battery such as a coin cell. In some embodiments, the power source 1322 can include an electrochemical fuel cell configured to perform a redox reaction on saliva to generate electrical power. In other embodiments, the power source 1322 can be configured to use kinetic power, for example, provided by movement of the jaw of the user during speaking or chewing. A memory 1325 is provided that can store instructions executable by a processor 1324 to perform the sensing and/or communication operations. The device 1300 also includes one or more communication devices. For example, the device 1300 can include a Bluetooth® transceiver 1326, a Wi-Fi transceiver 1328, an RFID or NFC tab 1330, a cellular transceiver 1332 and/or a GPS transceiver 1334. In particular embodiments, the processor 1324 can be to interpret signals from the Bluetooth® transceiver 1326, or any of the other transceivers described herein, provided by a user. The instructions can include, for example, firmware updates, sensor 1340 calibration parameters, device 1300 on/off, or any other instructions. The instructions can be input into an app (e.g., a smartphone app, a tablet app, a computer app, or a program on remote server) which are communicated to the processor 1324 and/or stored in the memory 1325 via the Bluetooth® transceiver 1326 or any of the other transceivers described herein. Similarly, the processor 1324 can also be to communicate information to the user (e.g., to a smartphone app, a tablet app, a computer app, or a program on remote server) via the Bluetooth® transceiver. Such information can include, for example, raw sensor 1340 data, processed data corresponding to one or more physical or biochemical parameters of the user measured from saliva which correspond to a health status of the user, device 1300 status (e.g., power remaining), sensor health data, or any other data providing overall information on diagnostic results and/or health of the user.

The sensor 1340 is configured to measure one or more physical and/or biochemical parameters of the user. The sensor 1340 can be substantially similar to the sensor 240, 740, 940, 1240 or any other sensor described herein and is therefore, not describe in further detail. In particular embodiments, an opening 1350 can be defined proximal to the sensor 1340 to allow saliva to access the sensor 1340. A porous matrix, for example, a polymer membrane, a silicone membrane, a hydrogel membrane, sol gel membrane, a cellulose membrane, or any other porous matrix can be positioned on the window to allow saliva to be communicated therethrough while preventing particulates, for example, food particles, which can damage the sensor 1340 or skew sensor 1340 measurements to pass therethrough.

Figure 14:
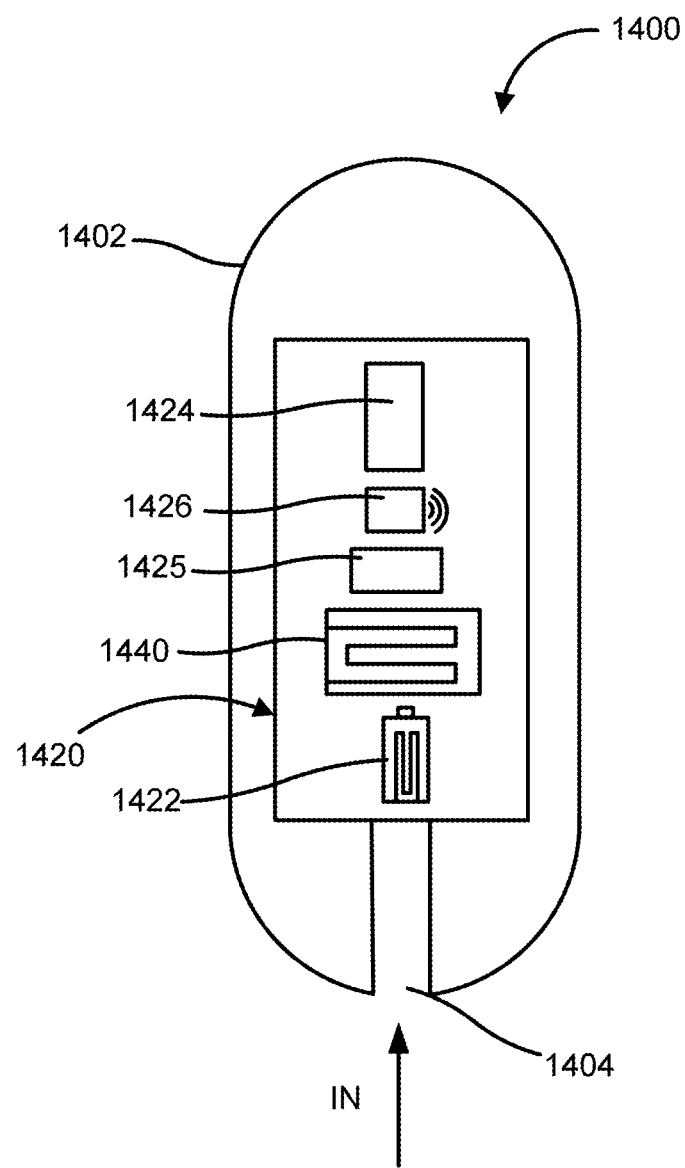
FIG. 14 is front view of an embodiment of an ingestible medical diagnostic device.

In some embodiments, a medical diagnostic device can include an ingestible pill. For example, FIG. 14 is a schematic illustration of a medical diagnostic device 1400 configured to be ingested by a user to measure one or more physical or biochemical parameters of the user. Such parameters can include, for example, glucose level, blood alcohol level (BAC), THC level (biomarker for marijuana), biomarkers for adrenal conditions (e.g., Cushing's disease, Addison's disease), hormone levels, altered female hormone states (e.g., PCOS, menopause, anovulation, pregnancy, irregular period cycles), altered male hormone states (e.g., hypogonadism, andropause, hyperestrogenic states), metabolic disorders (e.g., insulin resistance, diabetes, muscular dystrophy) benign and metastatic neoplasms (e.g., breast cancer, pancreatic cancer, prostate cancer, oral cancer, lung and throat cancer, etc.), infection diseases (e.g., HIV, viral hepatitis, flu, H1N1 flu, SARS virus, amoebiasis, heliobacter pylori infections, C. difficius infections, strep throat), food allergy, cortisol levels as indicators of stress, progesterone, or any other disease or medical condition for a which a biomarker is expressed in blood or digestive fluids.

The device 1400 includes a housing 1402 defining an internal volume. In some embodiments, the housing is non-biodegradable, i.e. does not dissolve or decompose within the digestive tract of the user. In such embodiments, an channel 1404 is defined in a sidewall of the housing 1402 to allow saliva or digestive fluids to enter the internal volume and access a sensor 1440 included in electronic circuitry 1420 of the device 1400. In other embodiments, the housing 1402 can be biodegradable which dissolves a predetermined time after ingestion to allow the digestive fluids to access the sensor 1440, as described in further detail herein. In such embodiments, the channel 1404 can be excluded.

The device includes the electronic circuitry 1420 which includes a power source 1422, a processor 1424, a memory 1425, a Bluetooth® transceiver 1426 and the sensor 1440 configured to perform any of the functions described herein. In various embodiments in which the housing 1402 is biodegradable, the electronic circuity 1420 and each of the components included therein can also be biodegradable, for example, formed from food grade and/or organic materials which are bio-degradable or bio-consumable. For example, the battery 1422 can be a biobattery configured to be powered by the digestive fluids of the user. In some embodiments, each of the components included in the electronic circuitry 1420 are configured to decompose a predetermined time after ingestion, the predetermined time allowing sufficient delay to perform meaningful sensing measurements via the sensor 1440 and communicate the measured data via the Bluetooth® transceiver to a remote server before the electronic circuitry 1420 and the components included therein degrades. In other embodiments in which the housing 1402 is non-biodegradable, the electronic circuitry 1420 can included conventional electronic components.

Figure 15:
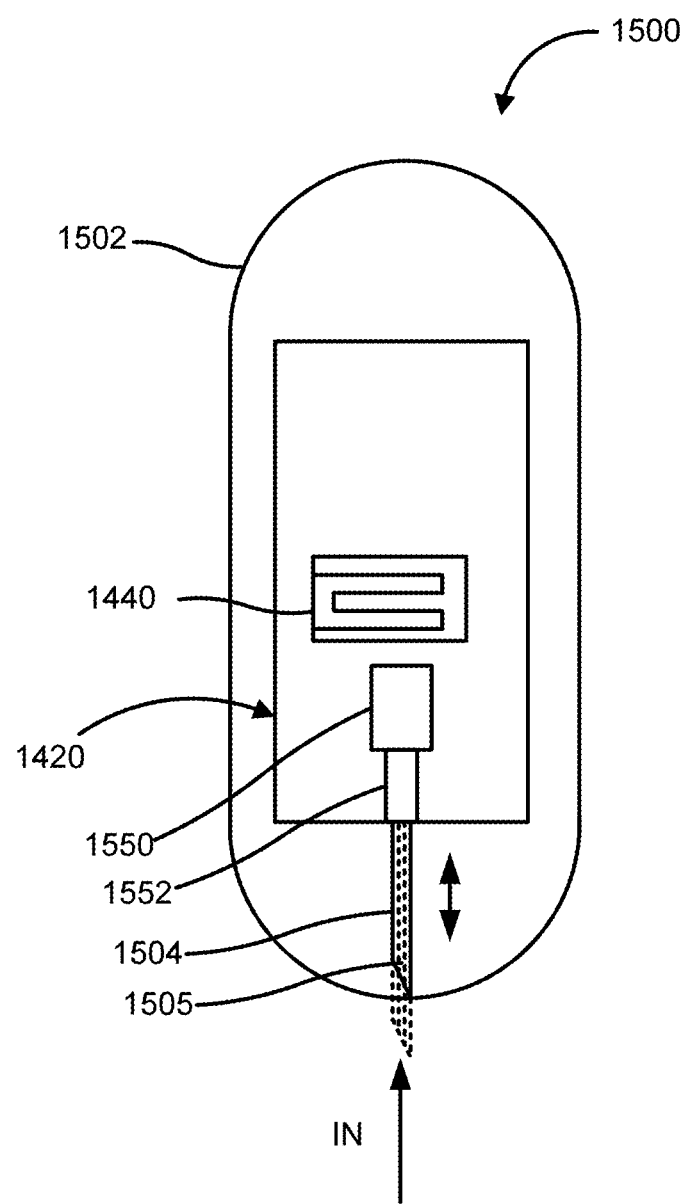
FIG. 15 is a front view of another embodiment of an ingestible medical diagnostic device.

In some embodiments, the device 1400 is configured to measure one or more physical or biochemical parameters, for example, BAC, from a saliva or digestive fluid of a user. In other embodiments, it might be necessary to obtain blood to perform reliable measurements. In such embodiments, an ingestible medical diagnostic device can include a needle to draw blood from within a digestive tract of the user. For example, FIG. 15 is a schematic illustration of another ingestible medical diagnostic device 1500. The device includes a housing 1502 defining an internal volume within which electronic circuitry 1402 that includes the sensor 1440 and is described with respect to the device 1400, is positioned. The housing 1502 is formed from a non-biodegradable material.

The device 1500 includes a needle 1504 defining a lumen 1505. The device 1500 also includes an actuator 1550 including a plunger 1552 configured to displace a tip of the needle proximal or distal relative to the housing 1502. The actuator 1550 can include a linear actuator, a gas pump actuator, or a spring loaded actuator. In some embodiments, a biasing member (not shown) can also be coupled to the needle to retract the needle 1504 into the housing 1502 once a blood sample is collected. For example, in an initial configuration, the needle 1504 can be positioned substantially within the housing 1502 such that the tip of the needle 1504 is within the housing 1502. At a predetermined time after ingestion of the device 1500 or after receiving a remote command from a user (e.g. via the Bluetooth® transceiver 1432 not shown in FIG. 15 for clarity), the actuator 1550 actuates the plunger 1552 to urge the tip of the needle 1504 distal from the housing 1502. The needle 1504 can pierce a sidewall of the housing 1504 or displace through an opening defined in a sidewall of the housing 1502 so that the tip of the needle 1504 emerges through the sidewall of the housing 1502 and pierces an endothelial lining of the digestive tract (e.g., duodenum, stomach, large intestine, small intestine, etc.) and draw a blood sample, for example, through capillary action. The blood is communicated via the lumen 1505 of the needle 1504 to the sensor 1440 for sensing. Once a sufficient amount of blood is withdrawn, the actuator 1550 can urge the plunger to withdraw the needle 1504 into the housing 1502 so that the tip is disposed substantially within the housing 1502. In other embodiments, a biasing member coupled to the needle 1504 can urge the needle 1504 into the housing 1502 once a sufficient amount of blood has been withdrawn.

FIG. 16 is a schematic flow diagram of an exemplary method for diagnosing one or more physical or biochemical parameters of a user using a medical diagnostic pill, for example, the medical diagnostic device 1500. The method includes initializing medical diagnostic pill activation at 1602, for example, activating the device 1500 before ingestion, placing the device 1500 in a buccal cavity, or remotely commanding the device 1500 to initialize. The medical diagnostic pill is orally ingested at 1604, for example, a user swallows the device 1500. A needle of the pill is actuated in response to one of elapse of a predetermined time or a remote actuation signal at 1606. For example, the processor 1424 of the electronic circuitry 1420 can be to include instructions for actuating the needle 1504 after a predetermined time has elapsed after swallowing to insert the tip of the needle into an endothelial layer of the digestive tract. In other embodiments, a remote actuation signal can be communicated via Bluetooth® or any other communication device using a smartphone app, a tablet app, or a program on a computer to actuate the needle.

Bodily fluid is drawn into a lumen of the needle and delivered to a sensor of the pill at 1608. For example, blood or interstitial fluid is drawn into the lumen 1505 of the needle 1504 when the tip of the needle 1504 is inserted into an endothelial layer of the digestive tract. The blood is communicated via the lumen 1505 to the sensor 1540. At least one biochemical parameter is sensed using the sensor at 1610, for example, the sensor 1440. The sensor data corresponding to the sensing of the parameter is communicated to a user 1612, for example, via the Bluetooth® transceiver 1432 included in the electronic circuitry 1420. In some embodiments, the needle is withdrawn in the housing of the pill after a sufficient quantity of blood has been drawn and communicated to the sensor 1540.

In certain embodiments, the electronic circuitry included in each of the medical diagnostic devices 200, 700, 900, 1200, 1300, 1400, 1500 or any other device described herein can include a diagnostic control system. The diagnostic control system may include a controller structured to perform certain operations to cause sensing or delivery of a substance. The controller may be a single device or a distributed device, and the functions of the controller may be performed by hardware and/or as computer instructions on a non-transient computer readable storage medium.

In certain embodiments, the controller includes one or more modules structured to functionally execute the operations of the controller. In certain embodiments, the controller includes sensor modules configured to measure time lapse, energy consumption, product consumption, rotation position, a change in rotation, linear position, a change in a linear position, product location, product ingredients, or other diagnostic, delivery or vaporization system operating parameters or conditions impacting the use, sensing, dispensing, or operation of the medical diagnostic system.

The description herein including modules emphasizes the structural independence of the aspects of the controller, and illustrates one grouping of operations and responsibilities of the controller. Other groupings that execute similar overall operations are understood within the scope of the present application. Modules may be implemented in hardware and/or as computer instructions on a non-transient computer readable storage medium, and modules may be distributed across various hardware or computer based components.

Example and non-limiting module implementation elements include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

Non-limiting examples of various embodiments are disclosed herein. Features from one embodiments disclosed herein may be combined with features of another embodiment disclosed herein as someone of ordinary skill in the art would understand.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A medical diagnostic and delivery device comprising:
a cartridge including one or more silos positioned in radial orientation about a central axis of the cartridge, each silo of the one or more silos including one or more substances or medicaments configured to be delivered to a user;
a heating element configured to vaporize the one or more substances to generate vapor for delivery to the user;
one or more sensors configured to generate measurements of the one or more substances or medicaments included within the cartridge;
a dipstick configured to receive saliva or breath of the user, and wherein the one or more sensors are configured to determine parameters associated with the saliva or breath of the user and
one or more processors coupled to memory and configured to:
select, based on the parameters, at least one of the one or more silos corresponding to the one or more substances or medicaments;
determine, from the measurements generated by the one or more sensors, an expiration date of the one or more substances or medicaments;
generate, based on the expiration date, an actuation request to rotate the cartridge about the central axis to position the one or more substances or medicaments for delivery to the user; and
generate, responsive to the expiration date indicating that the one or more substances or medicaments are unexpired, a vaporization request for the heating element to generate the vapor from the one or more substances or medicaments.

2. The medical diagnostic and delivery device of claim 1, wherein the one or more processors are further configured to generate, responsive to the expiration date indicating that the one or more substances or medicaments are expired, a repositioning request to rotate the cartridge to a different silo from the selected one or more silos.

3. The medical diagnostic and delivery device of claim 1, further comprising a communications device configured to:
transmit the parameters to a server; and receive, from the server responsive to the transmission, a selection of at least one of the one or more silos corresponding to the one or more substances or medicaments.

4. The medical diagnostic and delivery device of claim 3, wherein the heating element is configured to vaporize, responsive to the selection, the one or more substances or medicaments in the at least one of the one or more silos.

5. The medical diagnostic and delivery device of claim 1, wherein the one or more processors are further configured to transmit, while the heating element generates the vapor from the one or more substances or medicaments, to a display, the expiration date and the parameters on a display of the medical diagnostic and delivery device.

6. The medical diagnostic and delivery device of claim 1, further comprising:
a communications device configured to determine a location of the medical diagnostic and delivery device, and wherein the one or more processors configured to associate the location and the one or more substances or medicaments in the selected one or more silos.

7. The medical diagnostic and delivery device of claim 1, further comprising a microphone configured to receive an audio request to determine the expiration date of the one or more substances or medicaments.

8. A medical diagnostic and delivery device comprising:
a cartridge including one or more silos positioned in radial orientation about a central axis of the cartridge, each silo of the one or more silos including one or more substances or medicaments configured to be delivered to a user;
a heating element configured to vaporize the one or more substances to generate vapor for delivery to the user;
one or more sensors configured to generate measurements of the one or more substances or medicaments included within the cartridge, the cartridge is in fluidic communication with the one or more sensors, and wherein the one or more sensors are colorimetric sensors configured to generate an optical signal indicative of the expiration date of the one or more substances or medicaments; and
one or more processors coupled to memory and configured to:
determine, from the measurements generated by the one or more sensors, an expiration date of the one or more substances or medicaments; and
generate, based on the expiration date, an actuation request to rotate the cartridge about the central axis to position the one or more substances or medicaments for delivery to the user.

9. A method comprising:
obtaining, by one or more processors coupled to memory, from one or more inhalation sensors disposed on a dipstick disposed on a proximal end of the medical diagnostic and delivery device, parameters associated with saliva or breath of a user;
detecting, by the one or more processors, based on the parameters, a dispensing request to dispense one or more substances or medicaments disposed in one or more silos in a cartridge;
selecting, by the one or more processors, responsive to the dispensing request and based on the parameters, at least one of the one or more substances or medicaments;
identifying, by the one or more processors, at least one of the one or more silos corresponding to the selected one or more substances or medicaments; and
generating, by the one or more processors, a vaporization request for a heating element to vaporize the one or more substances or medicaments in the identified one or more silos.

10. The method of claim 9, wherein the cartridge includes the one or more silos positioned in radial orientation about a central axis of the cartridge and further comprising:
generating, by the one or more processors, an actuation request to rotate the cartridge about the central axis to position the selected one or more substances or medicaments for delivery to the user.

11. The method of claim 10, further comprising:
generating, by the one or more processors, a comparison between the selected one or more substances or medicaments and a candidate substance or medicament disposed in the selected one or more silos; and
generating, by the one or more processors, based on the comparison indicating a difference between the candidate substance or medicament and the selected one or more substances or medicaments, a repositioning request to rotate the cartridge to a different silo from the selected one or more silos.

12. The method of claim 9, further comprising:
generating, by the one or more processors, a transmission request for a communications device to transmit the parameters to a server; and
receiving, by the one or more processors, from the server responsive to the transmission, a selection of the at least one of the one or more silos corresponding to the one or more substances or medicaments.

13. The method of claim 9, further comprising:
determining, by the one or more processors, from location measurements of a communications device of the medical diagnostic and delivery device, a location of the medical diagnostic and delivery device; and
associating, by the one or more processors, the location and the one or more substances or medicaments in the selected one or more silos.

14. The method of claim 9, further comprising:
generating, by the one or more processors, an expiration request to determine an expiration date of the selected one or more substances or medicaments;
obtaining, by the one or more processors, responsive to the expiration request, from one or more substance sensors disposed within the medical diagnostic and delivery device, measurements of the selected one or more substances or medicaments;
determining, by the one or more processors, based on the measurements, the expiration date of the selected one or more substances or medicaments; and
generating, by the one or more processors, responsive to the expiration date indicating that the selected one or more substances or medicaments are unexpired, the vaporization request to vaporize the selected one or more substances or medicaments by the heating element disposed within the medical diagnostic and delivery device.

* * * * *